(12) United States Patent
Rothberg et al.

(10) Patent No.: US 11,224,878 B2
(45) Date of Patent: Jan. 18, 2022

(54) SUBSTRATES HAVING MODIFIED SURFACE REACTIVITY AND ANTIFOULING PROPERTIES IN BIOLOGICAL REACTIONS

(71) Applicant: Quantum-Si Incorporated, Guilford, CT (US)

(72) Inventors: Jonathan M. Rothberg, Guilford, CT (US); Jeremy Lackey, Guilford, CT (US); Guojun Chen, Sherborn, MA (US)

(73) Assignee: Quantum-Si Incorporated, Guilford, CT (US)

( * ) Notice: Subject to any disclaimer, the term of this patent is extended or adjusted under 35 U.S.C. 154(b) by 0 days.

(21) Appl. No.: 15/971,493

(22) Filed: May 4, 2018

(65) Prior Publication Data

US 2018/0326412 A1 Nov. 15, 2018

Related U.S. Application Data

(60) Provisional application No. 62/502,525, filed on May 5, 2017.

(51) Int. Cl.
| | | |
|---|---|---|
| *B01L 3/00* | (2006.01) | |
| *C12Q 1/6848* | (2018.01) | |
| *C09D 5/16* | (2006.01) | |
| *C09D 187/00* | (2006.01) | |
| *C09D 171/02* | (2006.01) | |

(52) U.S. Cl.
CPC .............. *B01L 3/508* (2013.01); *B01L 3/5085* (2013.01); *C09D 5/1662* (2013.01); *C09D 171/02* (2013.01); *C09D 187/005* (2013.01); *C12Q 1/6848* (2013.01); *B01L 2200/12* (2013.01); *B01L 2200/141* (2013.01);
(Continued)

(58) Field of Classification Search
None
See application file for complete search history.

(56) References Cited

U.S. PATENT DOCUMENTS

| | | |
|---|---|---|
| 4,659,481 A | 4/1987 | Chen |
| 5,106,730 A | 4/1992 | van Ness et al. |

(Continued)

FOREIGN PATENT DOCUMENTS

| | | |
|---|---|---|
| EP | 0 702 090 A2 | 3/1996 |
| EP | 2 743 535 A1 | 6/2014 |

(Continued)

OTHER PUBLICATIONS

Definition of Poloxamer 407 provided by wikipedia.com ([retrieved on Nov. 1, 2019]. Retrieved from the Internet: <URL: en.wikipedia.org/wiki/Poloxamer_407>). (Year: 2019).*

(Continued)

*Primary Examiner* — Robert T. Crow
(74) *Attorney, Agent, or Firm* — Wolf, Greenfield & Sacks, P.C.

(57) ABSTRACT

Methods of preparing surfaces of sample wells are provided. In some aspects, methods of preparing a sample well surface involve contacting the sample well with a block copolymer to form an antifouling overlay over a metal oxide surface of the sample well. In some aspects, methods of passivating and/or selectively functionalizing a sample well surface are provided.

16 Claims, 10 Drawing Sheets

(52) U.S. Cl.
CPC ... *B01L 2300/0819* (2013.01); *B01L 2300/16* (2013.01); *B01L 2300/165* (2013.01)

(56) References Cited

U.S. PATENT DOCUMENTS

| | | | |
|---|---|---|---|
| 5,185,243 A | 2/1993 | Ullman et al. | |
| 5,194,370 A | 3/1993 | Bellinger et al. | |
| 5,707,804 A | 1/1998 | Mathies et al. | |
| 5,851,840 A | 12/1998 | Sluka et al. | |
| 6,153,442 A | 11/2000 | Pirio et al. | |
| 6,248,518 B1 | 6/2001 | Parkhurst et al. | |
| 6,255,083 B1 | 7/2001 | Williams | |
| 6,264,825 B1 | 7/2001 | Blackburn et al. | |
| 6,429,258 B1 | 8/2002 | Morgan et al. | |
| 6,517,776 B1 | 2/2003 | Rodgers et al. | |
| 6,762,048 B2 | 7/2004 | Williams | |
| 6,787,308 B2 | 9/2004 | Balasubramanian et al. | |
| 6,846,638 B2 | 1/2005 | Shipwash | |
| 6,869,764 B2 | 3/2005 | Williams et al. | |
| 6,936,702 B2 | 8/2005 | Williams et al. | |
| 7,052,847 B2 | 5/2006 | Korlach et al. | |
| 7,056,661 B2 | 6/2006 | Korlach et al. | |
| 7,229,799 B2 | 6/2007 | Williams | |
| 7,361,466 B2 | 4/2008 | Korlach et al. | |
| 7,399,590 B2 | 7/2008 | Piepenburg et al. | |
| 7,442,412 B2 | 10/2008 | Miller | |
| 7,928,038 B2 | 4/2011 | Menchen et al. | |
| 7,968,702 B2 | 6/2011 | Wegener et al. | |
| 8,034,623 B2 | 10/2011 | Oh et al. | |
| 8,084,734 B2 | 12/2011 | Vertes et al. | |
| 8,153,375 B2 | 4/2012 | Travers et al. | |
| 8,173,198 B2 | 5/2012 | Menchen et al. | |
| 8,192,961 B2 | 6/2012 | Williams | |
| 8,252,910 B2 | 8/2012 | Korlach et al. | |
| 8,257,954 B2 | 9/2012 | Clark et al. | |
| 8,309,330 B2 | 11/2012 | Travers et al. | |
| 8,354,252 B2 | 1/2013 | Wegener et al. | |
| 8,420,366 B2 | 4/2013 | Clark et al. | |
| 8,455,193 B2 | 6/2013 | Travers et al. | |
| 8,530,154 B2 | 9/2013 | Williams | |
| 8,581,179 B2 | 11/2013 | Franzen | |
| 8,846,881 B2 | 9/2014 | Korlach et al. | |
| 8,906,614 B2 | 12/2014 | Wegener et al. | |
| 8,927,212 B2 | 1/2015 | Kong et al. | |
| 8,980,584 B2 | 3/2015 | Williams | |
| 9,062,091 B2 | 6/2015 | Bjornson et al. | |
| 9,404,146 B2 | 8/2016 | Travers et al. | |
| 9,435,810 B2 | 9/2016 | Havranek et al. | |
| 9,464,107 B2 | 10/2016 | Wegener et al. | |
| 9,542,527 B2 | 1/2017 | Travers et al. | |
| 9,551,031 B2 | 1/2017 | Korlach et al. | |
| 9,551,660 B2 | 1/2017 | Kong et al. | |
| 9,566,335 B1 | 2/2017 | Emili et al. | |
| 9,582,640 B2 | 2/2017 | Travers et al. | |
| 9,600,626 B2 | 3/2017 | Travers et al. | |
| 9,606,058 B2 | 3/2017 | Rothberg et al. | |
| 9,617,594 B2 | 4/2017 | Rothberg et al. | |
| 9,678,012 B2 | 6/2017 | Rothberg et al. | |
| 9,678,080 B2 | 6/2017 | Bjornson et al. | |
| 9,696,258 B2 | 7/2017 | Rothberg et al. | |
| 9,719,073 B2 | 8/2017 | Emig et al. | |
| 9,759,658 B2 | 9/2017 | Rothberg et al. | |
| 9,784,679 B2 | 10/2017 | Rothberg et al. | |
| 9,845,501 B2 | 12/2017 | Williams | |
| 9,863,880 B2 | 1/2018 | Rothberg et al. | |
| 9,879,319 B2 | 1/2018 | Korlach et al. | |
| 9,910,956 B2 | 3/2018 | Travers et al. | |
| 9,921,157 B2 | 3/2018 | Rothberg et al. | |
| 9,957,291 B2 | 5/2018 | Sebo et al. | |
| 9,983,135 B2 | 5/2018 | Rothberg et al. | |
| 10,023,605 B2 | 7/2018 | Bjornson et al. | |
| 10,048,208 B2 | 8/2018 | Rothberg et al. | |
| 10,066,258 B2 | 9/2018 | Kong et al. | |
| 10,150,872 B2 | 12/2018 | Zheng et al. | |
| 10,161,002 B2 | 12/2018 | Korlach et al. | |
| 10,174,363 B2 | 1/2019 | Rothberg et al. | |
| 10,481,162 B2 | 11/2019 | Emili et al. | |
| 10,544,449 B2 | 1/2020 | Shen et al. | |
| 10,545,153 B2 | 1/2020 | Marcotte et al. | |
| 10,570,445 B2 | 2/2020 | Kong et al. | |
| 10,676,788 B2 | 6/2020 | Shen et al. | |
| 10,731,209 B2 | 8/2020 | Ball et al. | |
| 10,745,750 B2 | 8/2020 | Korlach et al. | |
| 10,787,573 B2 | 9/2020 | Zheng et al. | |
| 2003/0077452 A1* | 4/2003 | Guire ................ A61L 27/34 428/412 |
| 2004/0009300 A1 | 1/2004 | Shimakura et al. | |
| 2005/0042633 A1 | 2/2005 | Williams | |
| 2005/0266456 A1 | 12/2005 | Williams et al. | |
| 2005/0277780 A1 | 12/2005 | Gordon et al. | |
| 2006/0234901 A1 | 10/2006 | Scheuing et al. | |
| 2007/0072196 A1 | 3/2007 | Xu et al. | |
| 2007/0197890 A1* | 8/2007 | Boock ................ A61B 5/0031 600/365 |
| 2007/0219367 A1 | 9/2007 | Shchepinov et al. | |
| 2008/0032301 A1 | 2/2008 | Rank et al. | |
| 2008/0241512 A1 | 10/2008 | Boris et al. | |
| 2009/0263802 A1 | 10/2009 | Drmanac | |
| 2010/0009872 A1 | 1/2010 | Eid et al. | |
| 2010/0029494 A1 | 2/2010 | Cherkasov et al. | |
| 2010/0035254 A1 | 2/2010 | Williams | |
| 2011/0003343 A1 | 1/2011 | Nikiforov et al. | |
| 2011/0281776 A1 | 11/2011 | Eshoo et al. | |
| 2012/0322692 A1 | 12/2012 | Pham et al. | |
| 2013/0296195 A1 | 11/2013 | Gray et al. | |
| 2013/0316912 A1 | 11/2013 | Bjornson et al. | |
| 2015/0141267 A1 | 5/2015 | Rothberg et al. | |
| 2015/0141268 A1 | 5/2015 | Rothberg et al. | |
| 2015/0177150 A1 | 6/2015 | Rothberg et al. | |
| 2015/0299848 A1 | 10/2015 | Haukka et al. | |
| 2016/0041095 A1 | 2/2016 | Rothberg et al. | |
| 2016/0133668 A1 | 5/2016 | Rothberg et al. | |
| 2016/0341664 A1 | 11/2016 | Rothberg et al. | |
| 2016/0344156 A1 | 11/2016 | Rothberg et al. | |
| 2016/0369332 A1 | 12/2016 | Rothberg et al. | |
| 2016/0370291 A1 | 12/2016 | Rothberg et al. | |
| 2016/0370292 A1 | 12/2016 | Rothberg et al. | |
| 2016/0377543 A1 | 12/2016 | Rothberg et al. | |
| 2016/0380025 A1 | 12/2016 | Rothberg et al. | |
| 2017/0107562 A1 | 4/2017 | Rothberg et al. | |
| 2017/0136433 A1 | 5/2017 | Sun et al. | |
| 2017/0349944 A1 | 12/2017 | Rothberg et al. | |
| 2017/0350818 A1 | 12/2017 | Rothberg et al. | |
| 2017/0362651 A1 | 12/2017 | Rothberg et al. | |
| 2018/0163312 A1 | 6/2018 | Blomberg et al. | |
| 2018/0208911 A1 | 7/2018 | Reed et al. | |
| 2018/0211003 A1 | 7/2018 | Travers et al. | |
| 2018/0217092 A1 | 8/2018 | Hinz et al. | |
| 2018/0223353 A1 | 8/2018 | Ball et al. | |
| 2018/0299460 A1 | 10/2018 | Emili | |
| 2018/0346507 A1 | 12/2018 | Sebo et al. | |
| 2019/0010183 A1 | 1/2019 | Bjornson et al. | |
| 2019/0017170 A1 | 1/2019 | Sharma et al. | |
| 2019/0249153 A1 | 8/2019 | Kamtekar et al. | |
| 2020/0141944 A1 | 5/2020 | Emili et al. | |
| 2020/0148727 A1 | 5/2020 | Tullman et al. | |
| 2021/0129179 A1 | 5/2021 | Chen et al. | |

FOREIGN PATENT DOCUMENTS

| | | |
|---|---|---|
| JP | S57-35678 A | 2/1982 |
| WO | WO 1996/21036 A2 | 7/1996 |
| WO | WO 2005/044836 A2 | 5/2005 |
| WO | WO 2005/093870 A1 | 10/2005 |
| WO | WO 2007/070572 A2 | 6/2007 |
| WO | WO 2010/065322 A1 | 6/2010 |
| WO | WO 2010/115016 A2 | 10/2010 |
| WO | WO 2011/049816 A2 | 4/2011 |
| WO | WO 2012/024500 A1 | 2/2012 |
| WO | WO 2013/158982 A1 | 10/2013 |
| WO | WO 2015/038954 A1 | 3/2015 |
| WO | WO 2016/187580 A1 | 11/2016 |
| WO | WO 2018/154572 A1 | 8/2018 |
| WO | WO 2018/170382 A1 | 9/2018 |

(56) References Cited

FOREIGN PATENT DOCUMENTS

| WO | WO 2018/204810 A1 | 11/2018 |
| WO | WO 2019/040825 A1 | 2/2019 |
| WO | WO 2020/102741 A1 | 5/2020 |

OTHER PUBLICATIONS

U.S. Appl. No. 15/847,001, filed Dec. 19, 2017, Ball et al.
PCT/US2018/031125, dated Jul. 9, 2018, International Search Report and Written Opinion.
PCT/US2017/067421, dated Mar. 6, 2018, International Search Report and Written Opinion.
PCT/US2017/067421, dated Jul. 4, 2019, International Preliminary Report on Patentability.
International Search Report and Written Opinion for International Application No. PCT/US2018/031125 dated Jul. 9, 2018.
International Search Report and Written Opinion for International Application No. PCT/US2017/067421 dated Mar. 6, 2018.
International Preliminary Report on Patentability for International Application No. PCT/US2017/067421 dated Jul. 4, 2019.
Heller, DNA Microarray Technology: Devices, Systems and Applications. Annu Rev Biomed Eng. 2002;4:129-53. Epub Mar. 22, 2002.
Nwe et al., Growing applications of "click chemistry" for bioconjugation in contemporary biomedical research. Cancer Biother Radiopharm. Jun. 2009;24(3):289-302. doi: 10.1089/cbr.2008.0626.
Thirumurugan et al., Click chemistry for drug development and diverse chemical-biology applications. Chem Rev. Jul. 10, 2013;113(7):4905-79. doi: 10.1021/cr200409f. Epub Mar. 27, 2013.
Tuske et al., The J-helix of *Escherichia coli* DNA polymerase I (Klenow fragment) regulates polymerase and 3'- 5'-exonuclease functions. J Biol Chem. Aug. 4, 2000;275(31):23759-68.
International Preliminary Report on Patentability for International Application No. PCT/US2018/031125 dated Nov. 14, 2019.
U.S. Appl. No. 17/067,184, filed Oct. 9, 2020, Chen et al.
EP 18794185.1, dated Jan. 11, 2021, Extended European Search Report.
PCT/US2020/055052, dated Feb. 4, 2021, Invitation to Pay Additional Fees.
PCT/US2020/055052, dated Mar. 26, 2021, International Search Report and Written Opinion.
Extended European Search Report for European Application No. 18794185.1 dated Jan. 11, 2021.
Invitation to Pay Additional Fees for Application No. PCT/US2020/055052 dated Feb. 4, 2021.
International Search Report and Written Opinion for International Application No. PCT/US2020/055052 dated Mar. 26, 2021.
Koushik et al., Cerulean, Venus, and VenusY67C FRET reference standards. Biophys J. Dec. 15, 2006;91(12):L99-L101. doi: 10.1529/biophysj.106.096206. Epub Oct. 13, 2006. PMID: 17040988; PMCID: PMC1779932.
Saito et al., Dual-labeled oligonucleotide probe for sensing adenosine via FRET: a novel alternative to SNPs genotyping. Chem Commun (Camb). Jun. 7, 2007;(21):2133-5. doi: 10.1039/b618465k. Epub Feb. 28, 2007. PMID: 17520113.
Sato et al., Polyproline-rod approach to isolating protein targets of bioactive small molecules: isolation of a new target of indomethacin. J Am Chem Soc. Jan. 31, 2007;129(4):873-80. doi: 10.1021/ja0655643. PMID: 17243824.
Stryer et al., Energy transfer: a spectroscopic ruler. Proc Natl Acad Sci U S A. Aug. 1967;58(2):719-26. doi: 10.1073/pnas.58.2.719. PMID: 5233469; PMCID: PMC335693.
Williams et al., An artificial processivity clamp made with streptavidin facilitates oriented attachment of polymerase-DNA complexes to surfaces. Nucleic Acids Res. Oct. 2008;36(18):e121. doi: 10.1093/nar/gkn531. Epub Aug. 22, 2008. PMID: 18723573; PMCID: PMC2566871.

\* cited by examiner

SUBSTRATES HAVING MODIFIED SURFACE REACTIVITY AND ANTIFOULING PROPERTIES IN BIOLOGICAL REACTIONS

RELATED APPLICATIONS

This application claims priority under 35 U.S.C. § 119(e) to U.S. Provisional Patent Application No. 62/502,525, filed May 5, 2017, which is hereby incorporated by reference in its entirety.

FIELD OF THE APPLICATION

The present application is directed generally to selectively modified substrate surface portions and methods of preparing the same. Aspects of the technology provided herein relate to altering the reactivity of one or more desired portions of a sample well surface. In some aspects, the disclosure provides methods of selectively modifying one or more surface portions of a sample well.

BACKGROUND

Microarrays are widely used as tools in single molecule analyses, including nucleic acid analysis, nucleic acid sequencing, gene expression analysis, genotyping, mutation analysis, peptide analysis, peptide sequencing, and drug screening. Generally formed on a surface of a glass, metal, plastic, or other substrate, microarrays can include selectively modified surface portions that are rendered to be more reactive or less reactive toward a desired chemical species. For example, single molecule analyses can require confinement of a molecule of interest to a desired region of the substrate for detection or observation. Where a population of non-specifically bound molecules are within such a region, it can be challenging to filter out interfering signals during analysis and can diminish accuracy of the results by contributing to the overall statistical analysis.

SUMMARY

Aspects of the technology disclosed herein relate to methods of generating a selectively functionalized portion of a sample well surface, and devices comprising the same. In some embodiments, methods of preparing a passivated surface portion of a sample well are provided herein. In some embodiments, the disclosure provides methods of preparing a passivated surface portion of a sample well having antifouling properties. In some embodiments, the disclosure relates to the passivation of a metal oxide surface portion of a sample well to promote selective functionalization of a silica surface portion of a sample well. In some embodiments, the technology provided in the present disclosure can be used to confine a molecule of interest to a desired region of a sample well.

In some aspects, the disclosure provides methods of selectively functionalizing a surface of a sample well that involve contacting a sample well having a first surface and a second surface with a block copolymer that preferentially binds a coating layer on the first surface. In some embodiments, the sample well is contacted with the block copolymer in an amount sufficient to form an antifouling overlay over the first surface. In some embodiments, the methods further involve contacting the sample well with a functionalizing agent that preferentially binds the second surface to generate a functionalized second surface, wherein the functionalizing agent comprises a coupling moiety. In some embodiments, the sample well is contacted with the block copolymer prior to being contacted with the functionalizing agent. In some embodiments, the sample well is contacted with the functionalizing agent prior to being contacted with the block copolymer.

In some embodiments, the first surface is a metal or metal oxide surface. In some embodiments, the first surface is a plastic surface (e.g., polyethylene, polypropylene, polystyrene, polycarbonate, polyvinyl chloride, polytetrafluoroethylene, or combinations thereof). In some embodiments, the second surface is a silica surface. In some embodiments, the first surface is a metal oxide surface and the second surface is a silica surface. In some embodiments, the coating layer comprises an amphipathic reagent.

In some aspects, the disclosure provides methods of functionalizing a silica surface of a sample well that involve contacting a sample well having a metal oxide surface and a silica surface with a block copolymer that preferentially binds a coating layer on the metal oxide surface. In some embodiments, the sample well is contacted with the block copolymer in an amount sufficient to form an antifouling overlay over the metal oxide surface. In some embodiments, the methods further involve contacting the sample well with a functionalizing agent that preferentially binds the silica surface to generate a functionalized silica surface. In some embodiments, the functionalizing agent comprises a coupling moiety. In some embodiments, the sample well is contacted with the block copolymer prior to being contacted with the functionalizing agent. In some embodiments, the sample well is contacted with the functionalizing agent prior to being contacted with the block copolymer.

In some embodiments, the methods further comprise contacting the sample well with an amphipathic reagent that preferentially binds the metal oxide surface to form the coating layer on the metal oxide surface. In some embodiments, the amphipathic reagent comprises a hydrophilic head group configured to preferentially bind the metal oxide surface and a hydrophobic tail group configured to preferentially bind the block copolymer.

In some embodiments, the hydrophilic head group comprises a sulfate, sulfite, phosphate, phosphonate, hydroxyl, catecholate, isocyanate, hydroxamate, or carboxyl functional group. In some embodiments, the hydrophilic head group comprises a carbonyl, amino, sulfhydryl, ether, ester, phosphodiester, glycosidic, or carboxamide functional group. In some embodiments, the hydrophobic tail group comprises a $C_1$-$C_{30}$ alkyl chain. In some embodiments, the hydrophobic tail group is selected from the group consisting of substituted or unsubstituted alkylene; substituted or unsubstituted alkenylene; substituted or unsubstituted alkynylene; substituted or unsubstituted heteroalkylene; substituted or unsubstituted heteroalkenylene; substituted or unsubstituted heteroalkynylene; substituted or unsubstituted heterocyclylene; substituted or unsubstituted carbocyclylene; substituted or unsubstituted arylene; substituted or unsubstituted heteroarylene; and combinations thereof. In some embodiments, the hydrophobic tail group comprises a polyfluorinated carbon chain.

In some embodiments, the amphipathic reagent comprises an alkyl phosphonic acid compound of formula $CH_3(CH_2)_nPO_3H_2$, where n is an integer with a value of 1-30. In some embodiments, the amphipathic reagent comprises hexylphosphonic acid, octylphosphonic acid, decylphosphonic acid, dodecylphosphonic acid, polyvinylphosphonic acid, 12-phosphono-1-dodecanesulfonic acid, 10-undecynylphosphonic acid, or heptadecafluorodecylphosphonic acid. In some embodiments, the amphipathic reagent comprises a fluorosurfactant. In some embodiments, the fluorosurfactant is a compound of formula $CF_3(CF_2)_nZ$, where n is an integer with a value of 1-30 and Z is a hydrophilic head group.

In some embodiments, the hydrophobic tail of the amphipathic reagent comprises a covalent coupling moiety. In such embodiments, the methods further comprise contacting the sample well with a polymeric compound that is configured to bind the covalent coupling moiety, thereby covalently attaching the polymeric compound to the amphipathic reagent on the metal oxide surface. In some embodiments, the amphipathic reagent comprises an alkyl phosphonic acid compound of formula $Y(CH_2)_nPO_3H_2$, where n is an integer with a value of 1-30, and Y is the covalent coupling moiety. In some embodiments, the covalent coupling moiety comprises an amine group, an azido group, a carboxyl group, a hydroxyl group, an alkyl group, an alkyne group, or a sulfhydryl group.

In some embodiments, the block copolymer is an A-B-A type block copolymer that comprises an A block and a B block. In some embodiments, the coating layer preferentially binds the B block of the A-B-A type block copolymer (e.g., to form the antifouling overlay). In some embodiments, the B block is more hydrophobic than the A block. In some embodiments, the A block comprises a first polyether block and the B block comprises a second polyether block that is more hydrophobic than the first polyether block.

In some embodiments, the A-B-A type block copolymer is a compound of Formula I:

where A is a monomeric unit of a polyether compound that comprises the A block; a is an integer with a value of 2-150; B is a monomeric unit of a polyether compound that comprises the B block; and b is an integer with a value of 10-100.

In some embodiments, the A block comprises polyethylene oxide and the B block comprises polypropylene oxide. In some embodiments, the A-B-A type block copolymer is a compound of Formula II:

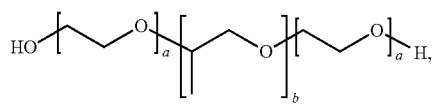

where a is an integer with a value of 2-150; and b is an integer with a value of 10-100.

In some embodiments, the metal oxide surface is aluminum oxide, titanium oxide, zirconium oxide, iron oxide, tin oxide, or tantalum oxide.

In some embodiments, the functionalizing agent comprises a silane compound. In some embodiments, the silane compound comprises mono-ethoxysilane, methoxysilane, di-ethoxysilane, trichlorosilane, or di-ethoxy, methoxysilane. In some embodiments, the silane compound comprises a silane-PEG compound. In some embodiments, the silane compound comprises a thiol-silane or an amino-silane compound.

In some embodiments, the coupling moiety of the functionalizing agent comprises a biotin molecule, an avidin protein, a streptavidin protein, a lectin protein, or a SNAP-TAG® (self-labeling protein tag). In some embodiments, the coupling moiety of the functionalizing agent comprises an amine group, an azido group, a carboxyl group, a hydroxyl group, an alkyl group, an alkyne group, or a sulfhydryl group.

In some embodiments, the methods further comprise contacting the sample well having the functionalized silica surface with a molecule of interest that is configured to bind the coupling moiety, under conditions suitable to permit binding of the molecule of interest to the coupling moiety, thereby coupling the molecule of interest to the functionalized silica surface.

In some embodiments, the contacting of the sample well with the molecule of interest occurs subsequent to the contacting of the sample well with the functionalizing agent without an intervening wash step. In some embodiments, the contacting of the sample well with the molecule of interest occurs subsequent to the contacting of the sample well with the block copolymer without an intervening wash step. In some embodiments, the sample well is contacted with the block copolymer and the functionalizing agent in separate contacting steps and without an intervening wash step.

In some embodiments, the molecule of interest comprises a polymerizing enzyme. In some embodiments, the polymerizing enzyme is a DNA polymerase. In some embodiments, the DNA polymerase is a T4 DNA polymerase. In some embodiments, the DNA polymerase is a T7 DNA polymerase. In some embodiments, the DNA polymerase is a phi29 DNA polymerase. In some embodiments, the DNA polymerase is an M2Y DNA polymerase. In some embodiments, the DNA polymerase is a DNA polymerase of *Lucilia cuprina*.

In some embodiments, the molecule of interest is a sequencing template complex that comprises a template nucleic acid molecule having a hybridized primer/polymerizing enzyme complex. In some embodiments, the template nucleic acid molecule is between about 1 kb to about 5 kb, between about 5 kb to about 10 kb, between about 10 kb to about 15 kb, between about 15 kb to about 20 kb, or between about 20 kb to about 25 kb. In some embodiments, the nucleic acid molecule is between about 25 kb to about 50 kb, between about 50 kb to about 100 kb, between about 100 kb to about 250 kb, between about 250 kb to about 500 kb, or between about 500 kb to about 1000 kb.

In some embodiments, the molecule of interest preferentially binds to the functionalized silica surface over the metal oxide surface (e.g., the metal oxide surface comprising the block copolymer and/or the coating layer) with about 100-fold to about 1000-fold selectivity, about 200-fold to about 800-fold selectivity, about 400-fold to about 600-fold selectivity, or about 1000-fold to about 2000-fold selectivity.

In some embodiments, selectivity of the molecule of interest for the functionalized silica surface over the metal oxide surface (e.g., the metal oxide surface comprising the block copolymer and/or the coating layer) is greater compared to a sample well not contacted with the block copolymer by about 10-fold to about 100-fold, about 50-fold to about 500-fold, about 100-fold to about 1000-fold, or about 200-fold to about 400-fold.

In some embodiments, methods provided herein further comprise subjecting the molecule of interest to a sequencing reaction. In some embodiments, methods provided herein further comprise subjecting the molecule of interest (e.g., a sequencing template complex) to a next generation sequencing technique.

In some aspects, the disclosure provides an integrated device that comprises a substrate (e.g., a solid support) comprising a sample well having a metal oxide surface and a silica surface. In some embodiments, the integrated device further comprises a coating layer on the metal oxide surface formed by an amphipathic reagent that comprises a hydrophilic head group and a hydrophobic tail group. In some embodiments, the amphipathic reagent is bound to the metal oxide surface through the hydrophilic head group. In some embodiments, the integrated device further comprises an antifouling overlay on the coating layer formed by an A-B-A type block copolymer that comprises an A block and a B block. In some embodiments, the A-B-A type block copolymer is bound to the coating layer through the B block. In some embodiments, the integrated device further comprises a functionalizing agent bound to the silica surface. In some embodiments, the functionalizing agent comprises a coupling moiety.

In some embodiments, the substrate comprises an array of sample wells, each sample well having a metal oxide surface and a silica surface.

In some embodiments, the sample well comprises a top aperture formed at a surface of the substrate and a bottom surface distal to the surface of the substrate. In some embodiments, the bottom surface is comprised by the silica surface.

In some embodiments, the coupling moiety of the functionalizing agent bound to the silica surface comprises a biotin molecule, an avidin protein, a streptavidin protein, a lectin protein, or a SNAP-TAG® (self-labeling protein tag). In some embodiments, the coupling moiety of the functionalizing agent bound to the silica surface comprises an amine group, an azido group, a carboxyl group, a hydroxyl group, an alkyl group, an alkyne group, or a sulfhydryl group.

In some embodiments, the integrated device is configured to interface with a next-generation sequencing instrument.

BRIEF DESCRIPTION OF THE DRAWINGS

The skilled artisan will understand that the figures, described herein, are for illustration purposes only. It is to be understood that, in some instances, various aspects of the invention may be shown exaggerated or enlarged to facilitate an understanding of the invention. In the drawings, like reference characters generally refer to like features, functionally similar and/or structurally similar elements throughout the various figures. The drawings are not necessarily to scale, emphasis instead being placed upon illustrating the principles of the teachings. The drawings are not intended to limit the scope of the present teachings in any way.

The features and advantages of the present invention will become more apparent from the detailed description set forth below when taken in conjunction with the drawings.

When describing embodiments in reference to the drawings, direction references ("above," "below," "top," "bottom," "left," "right," "horizontal," "vertical," etc.) may be used. Such references are intended merely as an aid to the reader viewing the drawings in a normal orientation. These directional references are not intended to describe a preferred or only orientation of an embodied device. A device may be embodied in other orientations.

As is apparent from the detailed description, the examples depicted in the figures (e.g., FIGS. 1-9) and further described for the purpose of illustration throughout the application describe non-limiting embodiments, and in some cases may simplify certain processes or omit features or steps for the purpose of clearer illustration.

Figure 1:
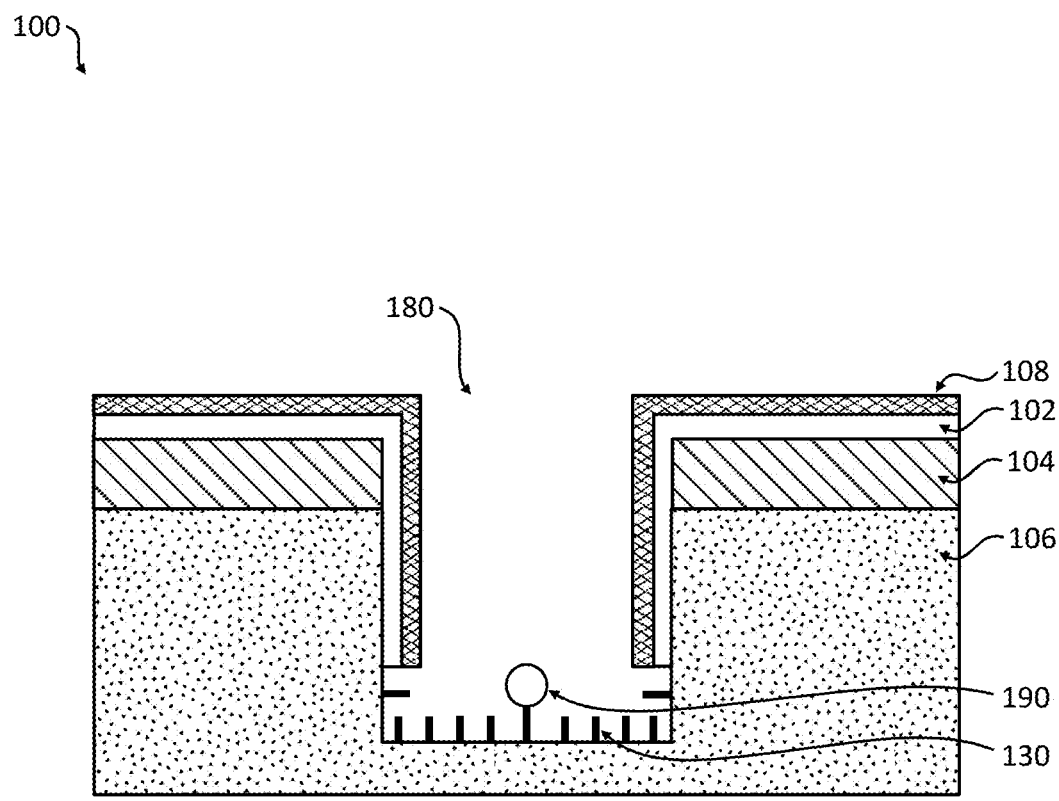

FIG. 1 depicts a cross-sectional view of a sample well.

Figure 2A:
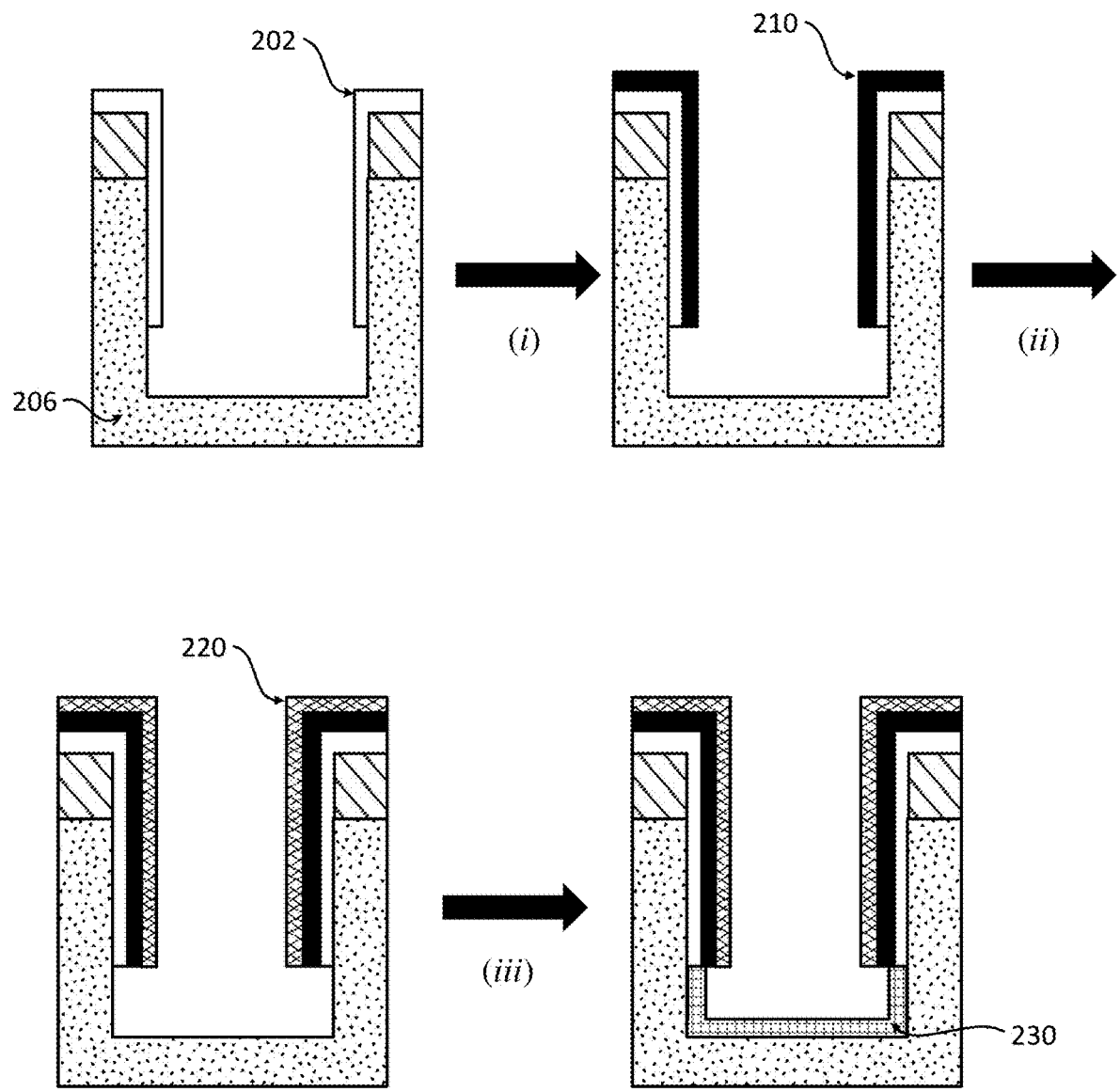
Figure 2B:
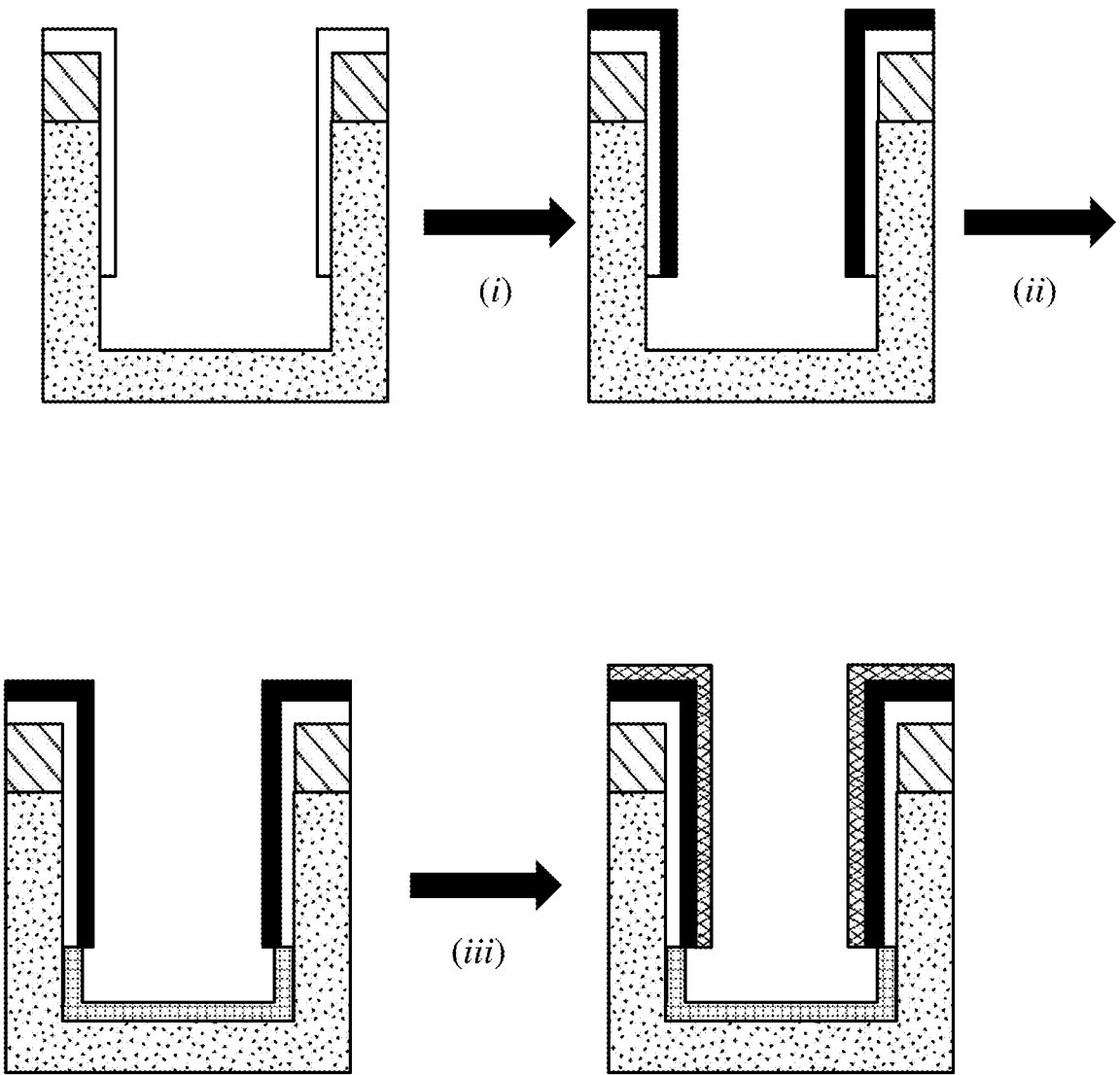

FIGS. 2A and 2B illustrate workflows for processes of selectively functionalizing a silica surface portion of a sample well.

Figure 3:
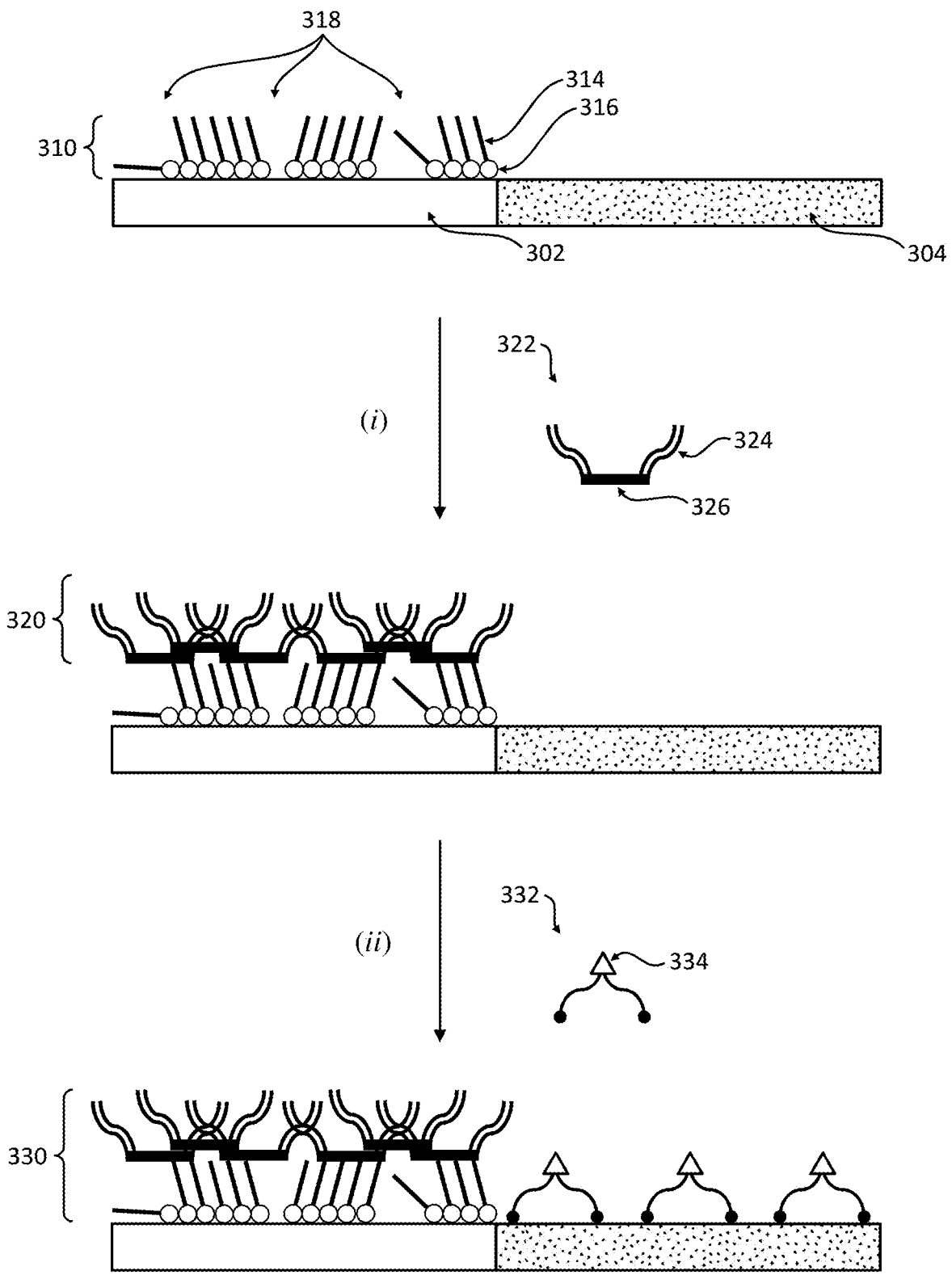

FIG. 3 depicts a process whereby a silica surface portion of a substrate is selectively functionalized by forming an antifouling overlay on a metal oxide surface portion of the substrate.

Figure 4:
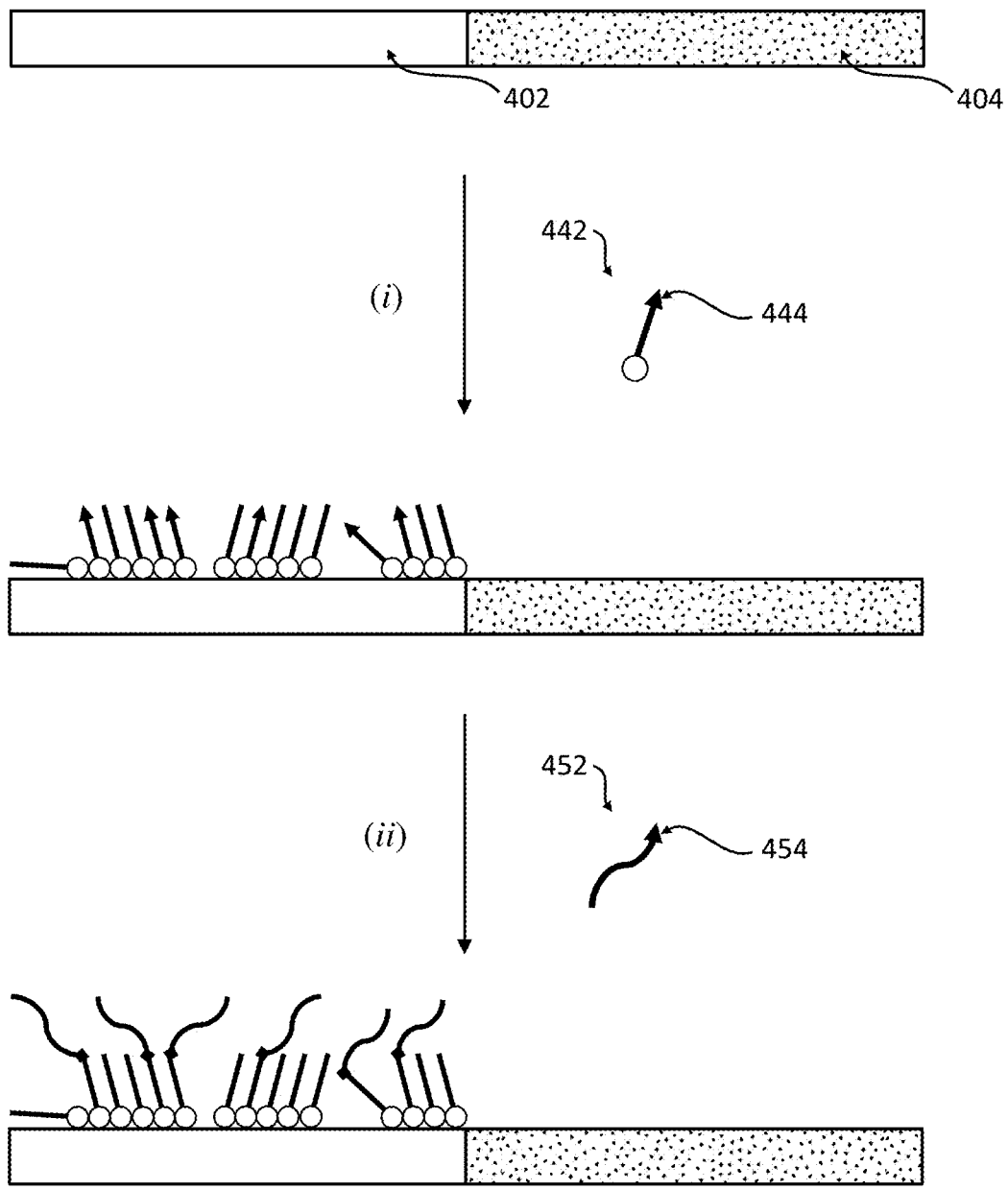

FIG. 4 depicts a process of passivating a metal oxide surface by generating a grafted polymer passivation layer on a metal oxide portion of a substrate.

Figure 5:
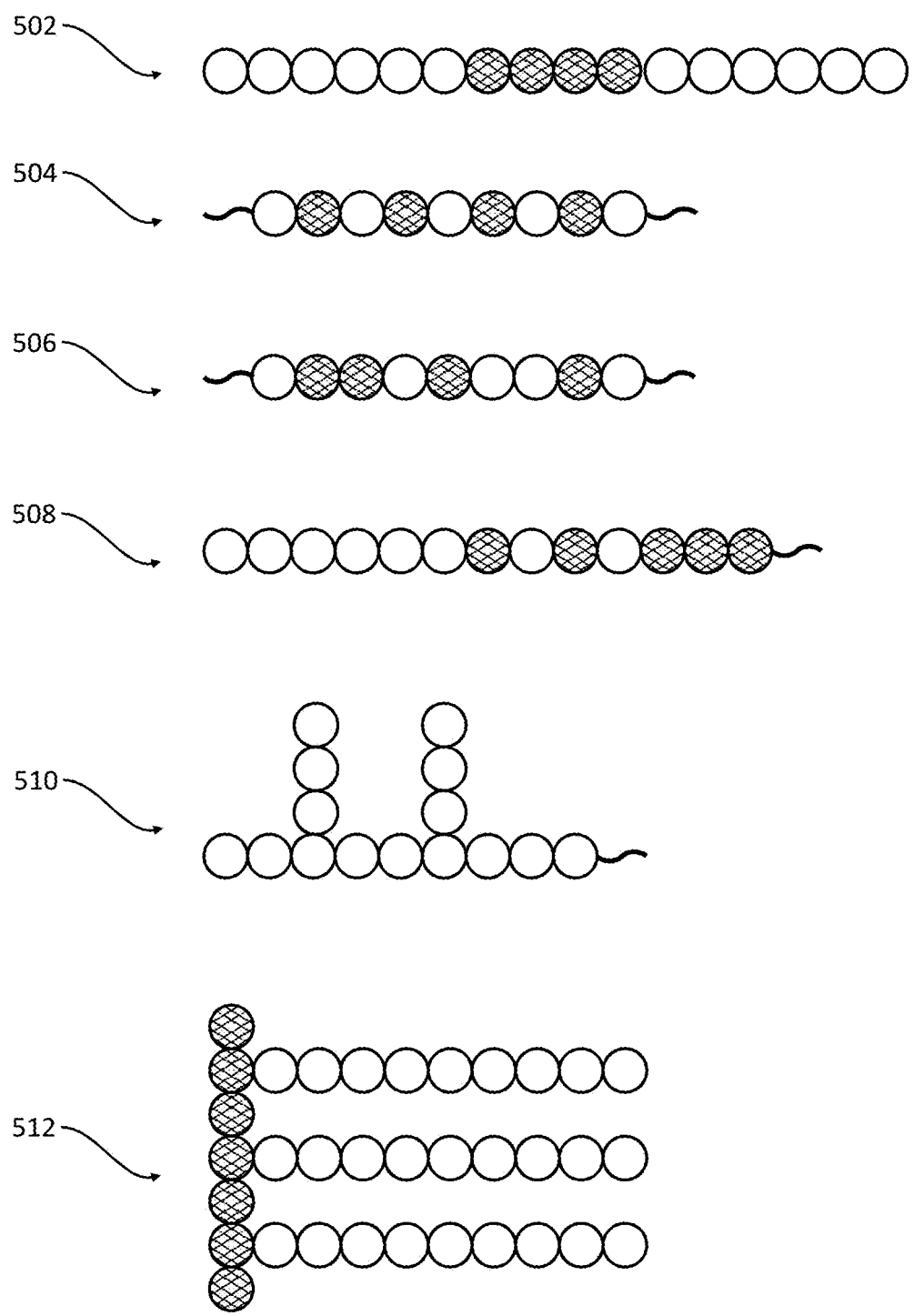

FIG. 5 depicts non-limiting configurations of block copolymers.

Figure 6:
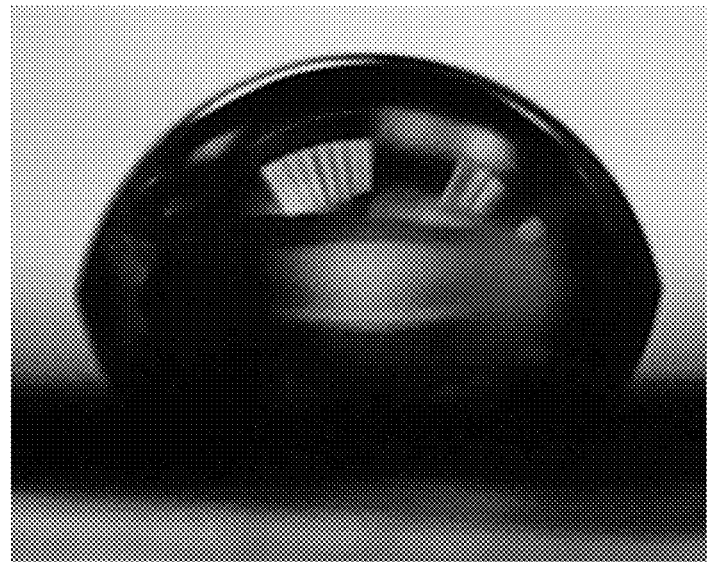
Figure 6:
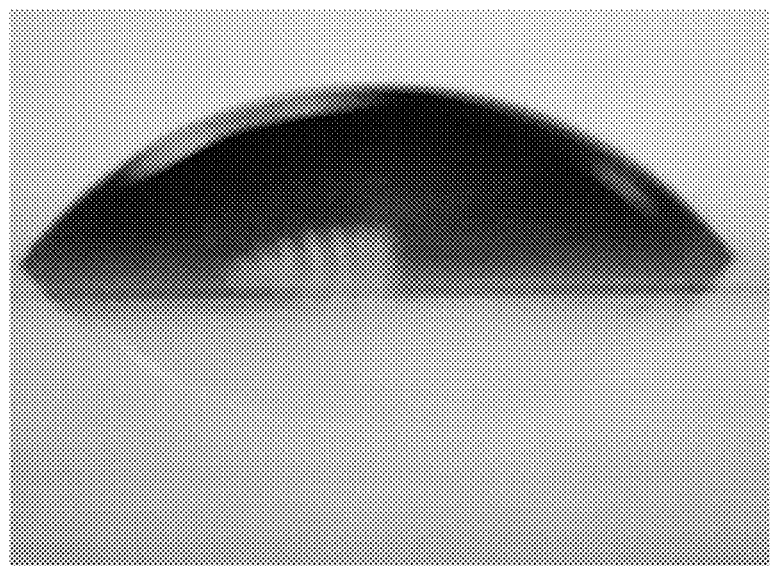

FIG. 6 provides imaging results from wettability experiments.

Figure 7:
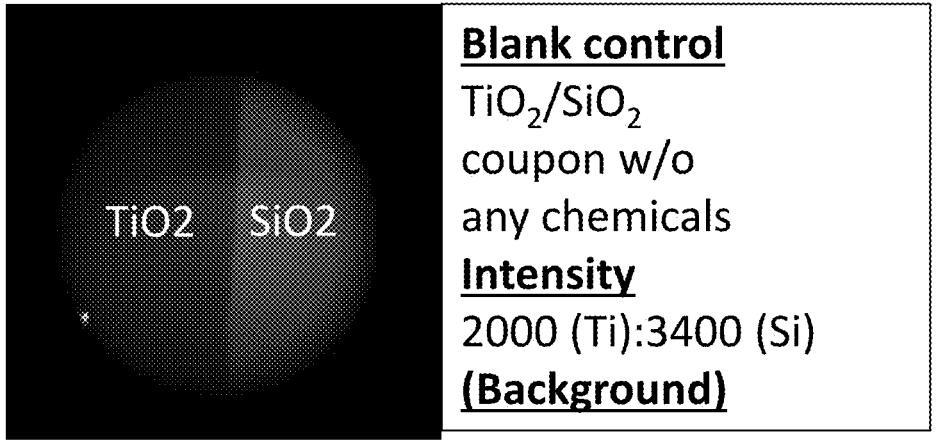
Figure 7:
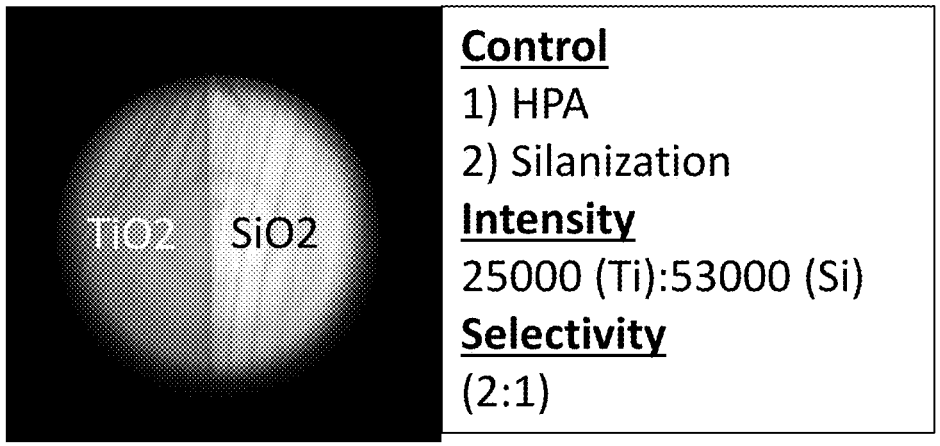
Figure 7:
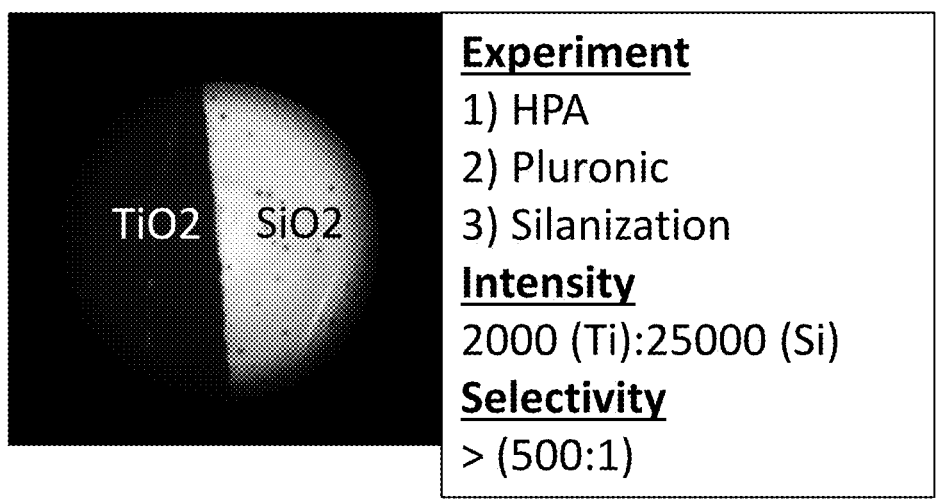

FIG. 7 provides imaging results from binding selectivity assays.

Figure 8:
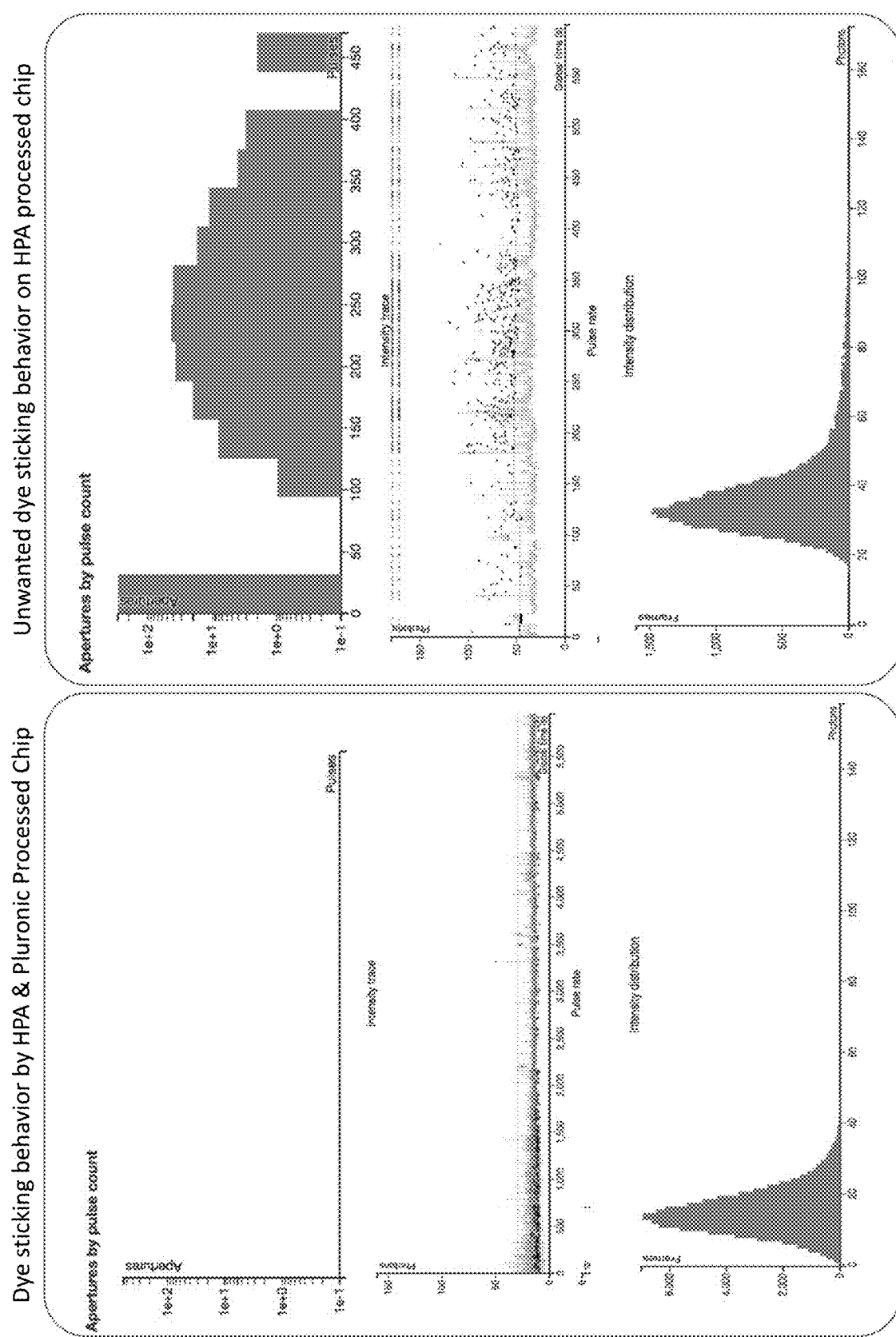

FIG. 8 depicts readouts and graphical representations of results obtained from fluorescence assays.

Figure 9:
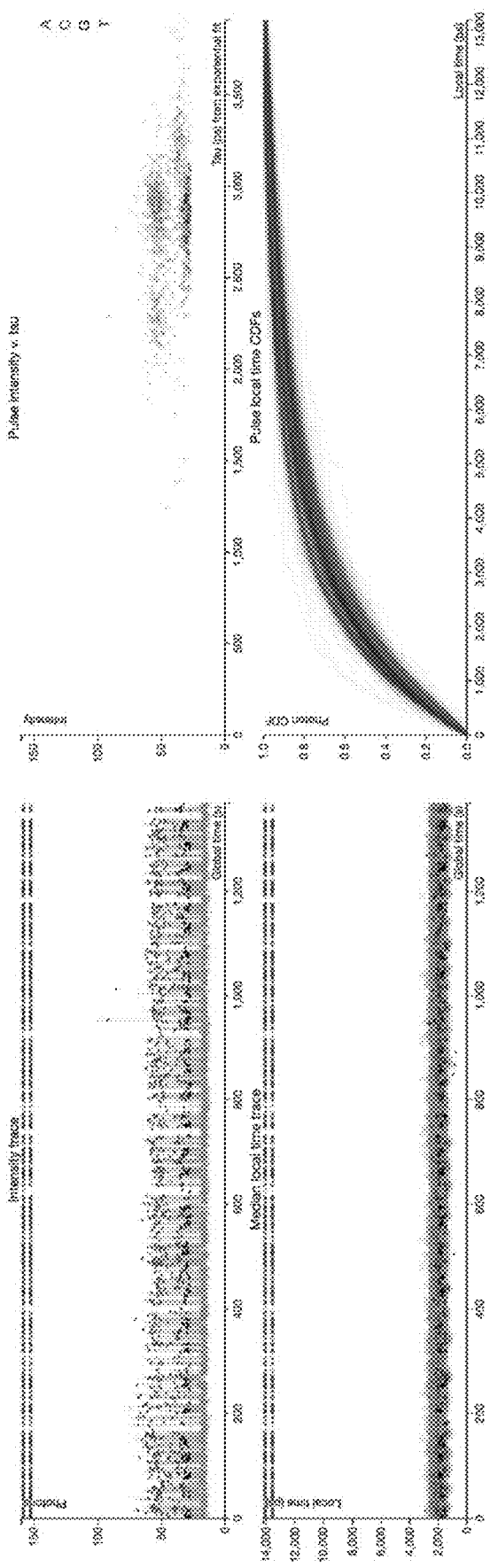

FIG. 9 depicts results from a sequencing reaction performed using an integrated device having a surface selectively functionalized in accordance with some embodiments described herein.

DETAILED DESCRIPTION

Aspects of the disclosure relate to sample wells having selectively modified surface portions, and methods of preparing the same. In some aspects, the disclosure provides methods of modifying surface portions of a sample well having a first surface portion and a second surface portion. In some embodiments, the sample well is contacted with an amphipathic reagent that preferentially binds the first surface portion to form a coating layer on the first surface portion. In some embodiments, the sample well is contacted with a block copolymer that preferentially binds a coating layer on the first surface portion (e.g., to form an antifouling overlay over the first surface portion). In some embodiments, the sample well is contacted with a functionalizing agent that preferentially binds the second surface portion to generate a functionalized second surface portion. In some embodiments, the first surface portion is a plastic surface and the second surface portion is a silica surface. In some embodiments, the first surface portion is a metal oxide surface and the second surface portion is a silica surface.

Among other aspects, the disclosure provides methods of preparing sample wells having selectively modified surface portions. In some embodiments, techniques provided herein can be used to passivate a metal oxide surface of a sample well having a surface portion composed of metal oxide and a surface portion composed of silica. In some embodiments, the disclosure provides methods of generating passivated metal oxide surfaces having antifouling properties. In some embodiments, passivated metal oxide surfaces described herein can be used to facilitate selective functionalization of the silica surface portion of the sample well. In some embodiments, the selectively modified surface portions of a sample well can be used to promote confinement of a molecule of interest to a desired region of the sample well.

In certain techniques, single molecule analysis involves confining a molecule of interest to a desired region of a sample well in which single molecule observation and/or signal detection is optimal. Confinement of the molecule of interest within the desired region can be achieved by selectively modifying surface portions of the sample well. For example, a surface portion in the desired region is functionalized to retain the molecule of interest, while a surface portion outside of the desired region is not functionalized. Such selective functionalization can be achieved by passivating the surface portion outside of the desired region, rendering it inert toward functionalization.

Surface passivation generally refers to a process whereby a surface is made to be less reactive toward an environment. For example, in some embodiments, where it may be desirable to selectively functionalize a second surface of a substrate over a first surface, the first surface can be passivated to render it incapable of, or highly resistant to, functionalization. Conventional surface passivation techniques can involve the use of compositions that form self-assembled monolayers, which commonly produce imperfectly covered surfaces due to various defects in the monolayer. These defects, in practice, provide sites of exposed surface at which functionalization can occur. The inventors have recognized and appreciated that these and other limitations can be overcome using reagents that effectively conceal monolayer defects. The inventors have further recognized and further appreciated that certain of these reagents confer antifouling properties on passivated surfaces that can be advantageously applied in the context of biological reactions.

Aspects of the disclosure relate to the selective modification of surface portions of sample wells. In some embodiments, a sample well comprises at least two surface portions having differing chemical compositions. For example, FIG. 1 depicts a cross-sectional view of a sample well 180 comprised by an integrated device 100, according to some non-limiting embodiments of the present application. The sample well 180 may comprise a small volume or region defined by an opening formed at a metal layer 104 and extending into a silica layer 106 of the integrated device 100. The sample well 180 may have one or more sidewalls covered, at least partially, with a metal oxide coating 102. In some embodiments, the metal oxide coating can be passivated, in accordance with the techniques described herein, to generate a passivation coating 108. The passivation coating 108, in some embodiments, can render the metal oxide coating 102 inert toward a functionalizing agent 130. In this way, the functionalizing agent 130 preferably binds to the silica layer 106. In some embodiments, the functionalizing agent 130 comprises a coupling moiety configured to bind a molecule of interest 190. Thus, the selectively functionalized surface of the silica layer 106 allows confinement of the molecule of interest 190 to a region proximate to the bottom surface of the sample well 180. In some embodiments, the passivation coating 108 includes a coating layer and/or an antifouling overlay to reduce the amount of molecule of interest 190 that interacts with or adheres to the sidewalls. In some embodiments, the coating layer and/or the antifouling overlay reduce or eliminate the adherence of components in a biological reaction to the sidewalls.

In some embodiments, a sample well having selectively modified surface portions can be prepared according to the workflow depicted in FIG. 2A. As shown, a sample well having a metal oxide surface 202 and a silica surface 206 is subjected to a passivation step (i) to generate a coating layer 210 on the metal oxide surface. In some embodiments, the coating layer 210 is formed by contacting the sample well with an amphipathic reagent that preferentially binds the metal oxide surface. The sample well may then be exposed to a block copolymer in step (ii) to generate an antifouling overlay 220 over the metal oxide surface. In some embodiments, the antifouling overlay 220 is formed by contacting the sample well with a block copolymer that preferentially binds the coating layer on the metal oxide surface. The sample well can further be subjected to a functionalization step (iii) to generate a functionalized silica surface 230. In some embodiments, the functionalized silica surface 230 is formed by contacting the sample well with a functionalizing agent that preferentially binds the silica surface.

It should be appreciated that, in some embodiments, the order of steps in the process of FIG. 2A can differ from that shown. For example, in some embodiments, a sample well having selectively modified surface portions can be prepared according to the workflow depicted in FIG. 2B. As shown, a sample well having a metal oxide surface and a silica surface is subjected to a passivation step (i) to generate a coating layer on the metal oxide surface. The sample well having the coating layer can further be subjected to a functionalization step (ii) to generate a functionalized silica surface. The sample well may then be exposed to a block copolymer in step (iii) to generate an antifouling overlay over the metal oxide surface. The processes shown in FIGS. 2A and 2B depict examples of a sample well having specific surface compositions, e.g., a metal oxide surface and a silica surface. It should be appreciated that, in some embodiments, techniques depicted in these figures and described elsewhere herein can be utilized with sample wells having different surface compositions. For example, in some embodiments, surface 202 can be a plastic surface. Examples of plastic surfaces include, by way of example and not limitation, polyethylene, polypropylene, polystyrene, polycarbonate, polyvinyl chloride, polytetrafluoroethylene, and combinations thereof.

In some embodiments, a functionalizing agent is capable of binding multiple surface compositions on a sample well, e.g., the functionalizing agent is capable of binding each of a metal oxide or silica surface composition. In such embodiments, techniques described herein can be advantageously used to restrict the binding of the functionalizing agent to a desired region or a specified surface composition of the sample well. For example, in some embodiments, a metal oxide surface of a sample well can be passivated to prevent or limit the extent of functionalization on the metal oxide surface—consequentially restricting functionalization to a different surface (e.g., a silica surface) of the sample well. In some embodiments, defects in a passivation coating can result in sites of exposed metal oxide surface, which can result in unwanted functionalization of the metal oxide surface. In some embodiments, techniques described herein are capable of concealing sites of exposed metal oxide surface in a passivation coating to promote functionalization of a silica surface with high selectivity.

In some aspects, methods described herein involve contacting a sample well having a metal oxide surface portion and a silica surface portion with a block copolymer that preferentially binds a coating layer on the metal oxide surface to form an antifouling overlay. In some embodiments, the antifouling overlay compensates for defects in the coating layer. In some embodiments, the coating layer comprises a monolayer. As used herein, a "monolayer" refers to a layer having a single-molecule thickness. In some embodiments, the term "monolayer" is used interchangeably with "self-assembled monolayer" ("SAM"), the latter of which refers to a process of self-assembly whereby molecules spontaneously form assemblies on surfaces by adsorption (e.g., chemisorption, physisorption). During this process of molecular assembly, defects may appear in the monolayer due to various intrinsic factors (e.g., thermodynamics of formation, chemical properties of the adsorbate) or external factors (e.g., imperfections on the surface, impurities). In some embodiments, defects in the monolayer result in sites of exposed surface. The present disclosure provides, in some embodiments, methods of concealing such defect sites using an antifouling overlay.

For example, FIG. 3 depicts a process in which an antifouling overlay is formed as part of a passivated metal oxide surface portion to allow a functionalizing agent to selectively bind to a silica surface portion. In some embodiments, a substrate (e.g., a sample well) having a metal oxide surface 302 and a silica surface 304 includes a coating layer 310 on the metal oxide surface 302. In some embodiments, the metal oxide surface 302 is composed of aluminum oxide, titanium oxide, zirconium oxide, iron oxide, tin oxide, or tantalum oxide. In some embodiments, the coating layer 310 is formed using an amphipathic reagent having a hydrophobic tail 314 and a hydrophilic head group 316 that preferentially binds the metal oxide surface 302. In some embodiments, the amphipathic reagent forms molecular assemblies on the metal oxide surface 302. As shown, in some embodiments, one or more defects 318 can form in the monolayer during self-assembly of the coating layer 310 formed by the amphipathic reagent. In some embodiments, the substrate (e.g., sample well) is subjected to a passivation step (i) that involves contacting the substrate with a block copolymer 322 that preferentially binds the coating layer 310 on the metal oxide surface 302 to form an antifouling overlay 320 over the metal oxide surface 302. In some embodiments, the nature and/or extent of the interactions formed between the block copolymer and the coating layer effectively cover the defect sites, as illustrated in FIG. 3.

In some embodiments, the block copolymer 322 is an A-B-A type block copolymer having an A block 324 and a B block 326. In some embodiments, the coating layer 310 preferentially binds the B block 326 of the A-B-A type block copolymer. In some embodiments, the B block 326 is hydrophobic relative to the A block 324. In such embodiments, the B block 326 can form interactions with the hydrophobic tail groups 314 of the coating layer 310 based on the hydrophobic effect. The hydrophobic effect generally refers to the tendency of non-polar molecules to aggregate in aqueous solution and exclude water molecules. Accordingly, as the hydrophobic tail groups 314 of the coating layer 310 are otherwise exposed to aqueous solvent, the coating layer 310 preferentially associates with the block copolymer 322 at the more hydrophobic B block 326. In some embodiments, the B block is more hydrophobic than the A block, and A and B have suitable respective degrees of polymerization, such that a critical micelle concentration of between or equal to 0.01 wt % and 10 wt % (e.g., between or equal to 0.01 wt % and 1 wt %) in aqueous solution exists at 25 degrees Celsius. The term "critical micelle concentration" has its ordinary meaning in the art and may refer to the concentration at and above which stable micelles (e.g., persistent micelles) form for certain ratios of (degree of polymerization of the A block) to (degree of polymerization of the B block). Critical micelle concentration can be measured by methods known to those of skill in the art and include but are not limited to surface tension measurements or dynamic light scattering measurements. In some embodiments, the additional coverage of exposed metal oxide surface 302 provided by the antifouling layer 320 promotes selective functionalization of the silica surface 304.

As shown in FIG. 3, in some embodiments, methods described herein can include a step of contacting the substrate (e.g., the sample well) having the antifouling overlay 320 with a functionalizing agent 332 that preferentially binds the silica surface 304. In some embodiments, the functionalizing agent 332 is capable of binding either the metal oxide surface 302 or the silica surface 304. However, in some embodiments, the metal oxide surface 302 is prepared with a passivation layer 330 that prevents the functionalizing agent 332 from binding the metal oxide surface 302, invariably promoting its selective binding to the silica surface 304 to generate a functionalized silica surface. In some embodiments, the functionalizing agent 332 comprises a silane compound capable of binding to the silica surface 304. In some embodiments, the silane compound comprises mono-ethoxysilane, methoxysilane, di-ethoxysilane, trichlorosilane, or di-ethoxy, methoxysilane.

In some embodiments, the functionalizing agent 332 comprises a coupling moiety 334. In some embodiments, the coupling moiety 334 can be used to attach a molecule of interest to the silica surface 304. In some embodiments, the coupling moiety 334 can be a first partner of a non-covalent binding pair. In this way, in some embodiments, the molecule of interest comprising a second partner of the non-covalent binding pair can be attached to the silica surface 304 through a non-covalent attachment. In some embodiments, the coupling moiety 334 of the functionalizing agent 332 can be a biotin molecule, an avidin protein, a streptavidin protein, a lectin protein, or a SNAP-TAG® (self-labeling protein tag). In some embodiments, the coupling moiety 334 can be a first partner of a covalent binding pair (e.g., a reactive chemical group). In this way, in some embodiments, the molecule of interest comprising a second partner of the covalent binding pair can be attached to the silica surface 304 through a covalent attachment. In some embodiments, the coupling moiety 334 of the functionalizing agent 332 can be an amine group, an azido group, a carboxyl group, a hydroxyl group, an alkyl group, an alkyne group, or a sulfhydryl group. In some embodiments, the coupling moiety 334 is compatible with click chemistry conjugation techniques. Reactive chemical groups capable of conjugation in click chemistry are known in the art, e.g., New, K., et al. (2009) Cancer Biother. Radiopharm. 24(3): 289-302, Thirumurugan, P., et al. (2013) Chem. Rev. 113 (7):4905-4979, the contents of which are incorporated herein by reference in their entirety. In some embodiments, the process depicted in FIG. 3 further comprises a step of contacting the sample well with the amphipathic reagent to form the coating layer 310 on the metal oxide surface 302.

Amphipathic Reagents & Coating Layers

As used herein, an "amphipathic reagent" refers to a reagent that can be used to generate a coating layer on a metal oxide surface. In some embodiments, the amphipathic reagent is a molecule that is considered amphipathic because the molecule contains a first portion that is hydrophilic relative to a second portion, the latter of which is consequentially hydrophobic relative to the first portion. In some embodiments, the hydrophilic portion is water-soluble relative to the hydrophobic portion. In some embodiments, the hydrophobic portion is water-insoluble relative to the hydrophilic portion. In some embodiments, the amphipathic reagent contains a hydrophilic head group and a hydrophobic tail group.

An appropriate amphipathic reagent can be selected based on desired properties (e.g., polarity, hydrophobicity, hydrophilicity, size, structural rigidity, etc.) to promote monolayer self-assembly. For example, in some embodiments, the amphipathic reagent can be designed for a specific solvent system by varying the hydrophobicity of the hydrophobic tail group. In some embodiments, the amphipathic reagent comprises an alkyl phosphonic acid compound of formula $CH_3(CH_2)_nPO_3H_2$, where n is an integer with a value of 1-30. In some embodiments, the amphipathic reagent comprises hexylphosphonic acid, octylphosphonic acid, decylphosphonic acid, dodecylphosphonic acid, polyvinylphosphonic acid, 12-phosphono-1-dodecanesulfonic acid, 10-undecynylphosphonic acid, or heptadecafluorodecylphosphonic acid.

In some embodiments, the amphipathic reagent comprises a fluorosurfactant. In some embodiments, the fluorosurfactant is a compound of formula $CF_3(CF_2)_nZ$, where n is an integer with a value of 1-30 and Z is a hydrophilic head group. A fluorosurfactant, also sometimes referred to as a fluorinated surfactant or a perfluorinated alkylated substance, is a synthetic organofluorine compound having multiple fluorine atoms. In some embodiments, the fluorosurfactant can be any compound having at least one of a —$CF_2$—, —$CF_2CF_3$, or —$CF_3$ group. Suitable fluorosurfactants may be selected in view of surface compositions and other experimental conditions used in the methods described herein. For example, fluorosurfactants and properties thereof are described in copending U.S. Publication No.: US20060234901, the content of which is incorporated herein by reference in its entirety. Additional examples of fluorosurfactants and methods of synthesizing the same are described in U.S. Application No.: U.S. Ser. No. 09/570,853, the content of which is incorporated herein by reference in its entirety.

In some embodiments, a hydrophilic head group of an amphipathic reagent is a chemical group (e.g., a functional group) capable of associating with a metal oxide surface. In some embodiments, the hydrophilic head group is capable of chelating with a metal or metal oxide surface composition. An appropriate hydrophilic head group can be selected in view of the surface compositions present on a substrate (e.g., sample well). For example, a hydrophilic head group of an amphipathic reagent can be designed such that the head group preferentially binds to the desired surface to be passivated. Accordingly, in some embodiments, the hydrophilic head group is designed to preferentially bind a metal oxide surface over a silica surface. In some embodiments, the hydrophilic head group is capable of forming hydrogen bond donor interactions or hydrogen bond acceptor interactions with a water molecule. Examples of hydrophilic head groups include, without limitation, sulfate, sulfite, sulfonate, sulfur groups, phosphate, phosphonate, hydroxyl, catecholate, isocyanate, hydroxamate, carboxyl, amino groups, amide groups, carboxyl groups, and hydroxyl groups. It should be appreciated that chemical groups disclosed herein are not intended to be limited to a particular protonation state or oxidation state. Thus, for example, a "carboxyl group" as used herein refers to, inter alia, a carboxylic acid group (R—COOH) and a carboxylate group (R—COO$^-$).

In some embodiments, the hydrophobic tail group may be designed according to experiment-dependent conditions, such as solvent temperature, pH, and ionic strength. It is generally preferable that the hydrophobic tail group of an amphipathic reagent have a lower affinity for a metal or metal oxide surface of a substrate than hydrophilic head group of the amphipathic reagent. In some embodiments, the hydrophobic tail group is configured to preferentially interact with a desired block of a block copolymer. In some embodiments, it may be desirable to design a hydrophobic tail group such that it is not completely soluble under a given set of experimental conditions. For example, in some embodiments, limiting the aqueous solubility of a hydrophobic tail group promotes self-assembly of amphipathic reagents in forming the monolayer coating. In some embodiments, the hydrophobic tail group is a saturated or unsaturated, substituted or unsubstituted, cyclic, branched or unbranched aliphatic chain. In some embodiments, the aliphatic chain comprises 4 to 28 carbon atoms. In some embodiments, the hydrophobic tail group comprises a $C_1$-$C_{30}$ alkyl chain.

In some embodiments, the hydrophobic tail of the amphipathic reagent comprises a covalent coupling moiety. In such embodiments, the methods further comprise contacting the sample well with a polymeric compound that is configured to bind the covalent coupling moiety, thereby covalently attaching the polymeric compound to the amphipathic reagent on the metal oxide surface. For example, FIG. 4 depicts a non-limiting process for passivating a metal oxide surface. As shown, a substrate (e.g., a sample well) having a metal oxide surface 402 and a silica surface 404 is subjected to a first passivation step (i) that involves contacting the substrate with an amphipathic reagent 442 that comprises a covalent coupling moiety 444. In some embodiments, the amphipathic reagent comprises an alkyl phosphonic acid compound of formula Y($CH_2$)—$PO_3H_2$, where n is an integer with a value of 1-30, and Y is the covalent coupling moiety. In some embodiments, the covalent coupling moiety comprises an amine group, an azido group, a carboxyl group, a hydroxyl group, an alkyl group, an alkyne group, or a sulfhydryl group. The amphipathic reagent 442 self-assembles on the metal oxide surface 402 through a hydrophilic head group, which preferentially binds the metal oxide surface 402 over the silica surface 404. In some embodiments, the metal oxide surface 402 preferentially binds the hydrophilic head group over the covalent coupling moiety of the amphipathic reagent.

In some embodiments, as shown in FIG. 4, the substrate (e.g., the sample well) is further subjected to an additional passivation step (ii) that involves contacting the substrate with a polymeric compound 452 that is configured to bind the covalent coupling moiety 444 of the amphipathic reagent 442. In this way, the polymeric compound 452 is grafted to the amphipathic reagent 442 on the metal oxide surface 402 to provide a more dense surface coverage in monolayer formation that minimizes sites of exposed metal oxide surface. In some embodiments, the polymeric compound 452 comprises a polyether compound. Polymeric and polyether compounds are described herein. In some embodiments, the polymeric compound 452 is selected to confer the passivated metal oxide surface 402 with antifouling properties. In some embodiments, the polymeric compound 452 is selected to preferentially associate with a block copolymer, as described herein. In some embodiments, the polymeric compound 452 includes a moiety 454 that configures the polymeric compound 452 to bind the covalent coupling moiety 444. In some embodiments, the moiety 454 comprises an amine group, an azido group, a carboxyl group, a hydroxyl group, an alkyl group, an alkyne group, or a sulfhydryl group.

In some aspects, methods described herein can be used to passivate a metal oxide surface by forming a coating layer on the metal oxide surface. As used herein, a "coating layer" refers to a monolayer that forms directly on a metal oxide surface. In some embodiments, the coating layer is formed on the metal oxide surface by monolayer self-assembly. In some embodiments, the coating layer is an ordered or disordered monolayer. In some embodiments, the coating layer can be an ordered and densely packed monolayer. In some embodiments, the coating layer can be a homogenous or heterogenous monolayer. In some embodiments, the components used to form the coating layer are allowed to self-assemble on the metal oxide surface. While not wishing to be bound by theory, it is believed that monolayer self-assembly on the metal oxide surface occurs via free energy minimization. For example, the hydrophilic head groups of the amphipathic reagent may be preferentially attracted to the metal oxide surface, which promotes aggregation of the head groups on the metal oxide surface to achieve orderly assembly of a monolayer. The metal oxide surface may also be viewed as the template around which the head groups of the amphipathic reagent congregate, leaving the hydrophobic tail groups of the amphipathic reagent extending from the metal oxide surface. Accordingly, in some embodiments, the tail groups in the context of a coating layer are free to associate with a block copolymer to generate an antifouling overlay.

Antifouling Overlays & Block Copolymers

As used herein, an "antifouling overlay" refers to a composition that provides or increases the resistance to biological molecules of a surface of an article to which the composition is attached. For example, in some embodiments, an antifouling overlay over a sample well surface (e.g., metal oxide) may resist the adhesion of biomolecules, including proteins, nucleic acids, nucleotides, labeled nucleotides, cells, tissue, and/or other biological matter relative to the amount of adhesion to a reference substrate, that is, the same or an otherwise functionally equivalent substrate lacking the antifouling overlay. In some embodiments, an antifouling overlay over a sample well surface (e.g., metal oxide) may resist the adhesion of hydrophobic molecules, such as hydrophobic components used in biological reactions (e.g., dye molecules, dye-labeled nucleotides, nucleotides, nucleic acids, etc.). In some embodiments, the amount of adhesion will be decreased 20%, 30%, 40%, 50%, 60%, 70%, 80%, or more, for example, 85%, 90%, 95%, 99%, 99.5%, 99.9%, or more, relative to the reference substrate. In some embodiments, the antifouling overlay is substantially resistant to polymerizing enzymes and/or nucleic acids. In some embodiments, the antifouling overlay is substantially resistant to biological molecules present in a blood sample.

In some embodiments, the antifouling overlay forms over a metal oxide surface. In some embodiments, the antifouling overlay can form over the metal oxide surface by direct interactions with the metal oxide surface (e.g., chelation with a metal oxide composition). In some embodiments, the antifouling overlay can form over the metal oxide surface through interactions with one or more intervening layers. For example, in some embodiments, the antifouling overlay is formed over the metal oxide surface through interactions with a coating layer (e.g., a monolayer) on the metal oxide surface. In some embodiments, the antifouling overlay interacts with the coating layer due to a hydrophobic effect. The hydrophobic effect refers to the tendency of hydrophobic molecules to aggregate in aqueous solution and exclude water molecules. In some embodiments, antifouling properties are conferred on metal oxide surfaces by contacting a metal oxide surface having a coating layer with a block copolymer that preferentially binds the coating layer.

As used herein, a "block copolymer" refers to polymers having more than one polymeric block, each having a distinct structure from that of an adjacent block. The entire structure, encompassing all blocks, forms the block copolymer. Block copolymers with two or three distinct blocks are called diblock or triblock copolymers, respectively. In some embodiments, each block of a copolymer is represented by a letter (e.g., "A" block, "B" block, "C" block, etc.), where each letter denotes a block of the copolymer having a distinct structural composition which gives rise to distinct properties for that block of the copolymer. In some embodiments, each block is comprised of one or more types of monomeric or constitutional units that can be selected based on a desired property, such as hydrophobicity or hydrophilicity, to be conferred on that block relative to another block within the block copolymer. For example, in some embodiments, a block copolymer as described herein is an A-B-A type triblock copolymer having an A block and a B block, where the B block is hydrophobic relative to the A block. In some embodiments, a block copolymer as described herein is an A-B type diblock copolymer having an A block and a B block, where the B block is hydrophobic relative to the A block.

In some embodiments, a triblock copolymer has three distinct blocks, which may be of alternating hydrophilic (A) and hydrophobic (B) blocks. FIG. 5 generically depicts non-limiting configurations of block copolymers and portions thereof. As shown, an A-B-A type triblock copolymer 502 can include a B block comprised of a first set of monomeric units (hatched circles) flanked on each side by A blocks comprised of a second set of monomeric units (open circles). In some embodiments, the A-B-A type block copolymer can be represented by Formula I: $(A_a)(B_b)(A_a)$, where A is a monomeric unit of a polymeric structure that comprises the A block, a is the degree of polymerization of the A block and an integer with a value of 2-150, B is a monomeric unit of a polymeric structure that comprises the B block, and b is the degree of polymerization of the A block and an integer with a value of 10-100.

In some embodiments, either of the A or B blocks may, themselves, be a copolymer. For example, in some embodiments, an A block and/or a B block of a block copolymer can include two or more types of monomeric units. In some embodiments, the monomeric units can be present within the A block and/or the B block as alternating monomers 504. In some embodiments, the monomeric units can be present within the A block and/or the B block in a random configuration 506. In some embodiments, the chemical interface at copolymer junction may be tapered. For example, in some embodiments, an A block and a B block can be separated by a tapered interface 508 such that the monomeric units of the A block gradually transition to the monomeric units of the B block. Thus, it should be appreciated that, as used herein, the terms "A block" and "B block" can generally refer to blocks of a block copolymer having different relative hydrophobic/hydrophilic properties, and should not be construed as limiting either block to a specific monomeric unit.

In some embodiments, a schematic generalization of a triblock copolymer can be represented by the formula $[A_aB_bC_c \ldots]_a[X_xY_yZ_z \ldots]_b[A_aB_bC_c \ldots]_a$, where each letter stands for a monomeric unit, each subscript to a monomeric unit represents the mole fraction of that unit in the particular block, the three dots indicate that there may be more or fewer monomeric units in each block, and a and b indicate the degrees of polymerization of the A and B blocks, respectively. As suggested by the schematic, in some embodiments, the number and the nature of each constitutional unit can be separately controlled for each block. The schematic is not meant and should not be construed to infer any relationship whatsoever between the number of constitutional units or the number of different types of constitutional units in each of the blocks, nor is the schematic meant to describe any particular number or arrangement of the constitutional units within a particular block. In each block the constitutional units may be disposed in a purely random, an alternating random, a regular alternating, a regular block, or a random block configuration unless expressly stated to be otherwise.

In some embodiments, a block copolymer can include a branched configuration. For example, FIG. 5 depicts an example of a branched block 510 of a block copolymer, where one or more monomeric units within a given block can be connected to more than two adjacent monomeric units. In some embodiments, a block copolymer as described herein can be configured as a brush copolymer 512. In this way, a first polymer block (shaded circles) can be designed to preferentially interact with a coating layer while a second polymer block (open circles) extends outward and can be designed to provide antifouling properties.

In some embodiments, at least one block (e.g., an A block and/or a B block) of a block copolymer comprises a composition having antifouling properties. In some embodiments, at least one block (e.g., an A block and/or a B block) of a block copolymer has an electrically neutral composition, a hydrophilic composition, and/or a composition comprising hydrogen bond donors but not hydrogen bond acceptors. In some embodiments, at least one block (e.g., an A block and/or a B block) of a block copolymer comprises a polyacrylate (e.g., a polyacrylate comprising urethane-linked side chains), an oligosaccharide, a polyurethane (e.g., a thermoplastic segmented polyurethane), or a polyether (e.g., a poly(ethylene glycol), a poly(ethylene oxide), a poly(propylene glycol), a poly(butylene glycol)), or a combination thereof. In some embodiments, each block (e.g., A blocks and B block(s)) of a block copolymer comprises a respective polyacrylate (e.g. a polyacrylate comprising urethane-linked side chains), an oligosaccharide, a polyurethane (e.g., a thermoplastic segmented polyurethane), or a polyether (e.g., a poly(ethylene glycol), a poly(ethylene oxide), a poly(propylene glycol), a poly(butylene glycol)), or a combination thereof.

In some embodiments, at least one block of a block copolymer is a polymeric structure that comprises a polyether. In some embodiments, each block of a block copolymer is a polymeric structure that comprises a polyether. In some embodiments, at least one block is an oligomeric structure or polymeric structure of monomeric units comprised of an ethylene oxide ($-CH_2CH_2O-$) repeat unit. In some embodiments, the A block comprises a first polyether block and the B block comprises a second polyether block that is more hydrophobic than the first polyether block. In some embodiments, the A block comprises polyethylene oxide and the B block comprises polypropylene oxide. In some embodiments, the A block and/or the B block comprise a mix of polyethylene oxide and polypropylene oxide, where the mix does not alter the B block's relative hydrophobicity compared to the A block. In some embodiments, the A-B-A type block copolymer is a compound of Formula II:

(Formula II)

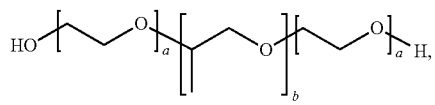

where a is an integer with a value of 2-150 and b is an integer with a value of 10-100. In some embodiments, a is a value of 10-30 inclusive, and b is a value of 40-100 inclusive. In some embodiments, a is a value of about 20, and b is a value of about 70. In some embodiments, a is a value of 80-120 inclusive, and b is a value of 35-95 inclusive. In some embodiments, a is a value of about 100, and b is a value of about 65.

In some embodiments, a block copolymer, such as a triblock copolymer, may have structural limitations to provide for a specific functional requirement. For example, the total molecular weight (e.g., a weight-average molecular weight, or a number-average molecular weight) of the block copolymer may be sufficiently low so that the polymer is a liquid at 25° C. or have a specified maximum viscosity at 25° C. In some embodiments, the total molecular weight (e.g., weight-average molecular weight) of the block copolymer may be determined using a goniometer to determine surface functionalization followed by analysis using time-of-flight secondary ion mass spectrometry. In some embodiments, the total molecular weight (e.g., weight-average molecular weight) of the block copolymer may be, for example, about 7,000 g/mol or less, or about 6,500 g/mol or less, or about 6,000 g/mol or less, or about 5,500 g/mol or less, or about 5,000 g/mol or less, or about, or about 4,500 g/mol or less, or about 4,000 g/mol or less, or about 3,500 g/mol or less, or about 3,000 g/mol, or about 2,500 g/mol or less, or about 2,000 g/mol or less, or about 1,500 g/mol or less, or about 1,000 g/mol or less. In some embodiments, the total molecular weight of the block copolymer is between 600 g/mol and 1,500 g/mol.

In some embodiments, the molecular weight of a specific block within the polymer may be specified to impart a specific characteristic to the block copolymer. For example, the molecular weight of the B block in an A-B-A type block copolymer can be varied relative to the total molecular weight of the block copolymer to alter the extent to which the B block interacts with the coating layer. A: 44.05 (881), B: 58.08 (4065). In some embodiments, the molecular weight of the B block can constitute between about 30% to about 40%, between about 40% to about 50%, between about 50% to about 60%, between about 60% to about 70%, between about 70% to about 80%, or more of the total molecular weight of the A-B-A type block copolymer.

Functionalization

In certain embodiments, techniques described herein can be used to confine a molecule of interest to a desired region of a sample well. In some embodiments, the desired region may be referred to as a "target volume" or a "reaction volume." In some embodiments, a sample well occupies a volume or space defined by an opening formed at a surface of an integrated device which extends through a first layer and into a second layer of the integrated device to a bottom surface distal to the opening. In some embodiments, the exposed surfaces of the first layer and second layer disposed between the opening and the bottom surface of the sample well may be referred to as sidewalls which further define the volume or space occupied by the sample well.

In some embodiments, the first layer is a metal cladding layer. In some embodiments, the metal cladding layer comprises one or more types of metals (e.g., aluminum, titanium, zirconium, iron, tin, tantalum, etc.). In some embodiments, the exposed surface portions of the first layer comprises a metal oxide. In some embodiments, the second layer is a transparent material or glass. In some embodiments, the exposed surface portions of the second layer comprises fused silica or silicon dioxide. In some embodiments, the sidewalls of the sample well are composed of at least a portion of each of the exposed surface portions of the first and second layers. In some embodiments, the bottom surface of the sample well comprises silica. In some embodiments, at least a portion of the sidewalls adjacent to the bottom surface comprises silica.

In embodiments when one or more molecule or complex (e.g., a sequencing template) is immobilized on the bottom surface, it may be desirable to functionalize the bottom surface to allow for attachment of one or more molecules or complexes. In certain embodiments, the bottom surface comprises a transparent glass. In certain embodiments, the bottom surface comprises fused silica or silicon dioxide. In some embodiments, the bottom surface is functionalized with a silane. In some embodiments, the bottom surface is functionalized with an ionically charged polymer. In some embodiments, the ionically charged polymer comprises poly (lysine). In some embodiments, the bottom surface is functionalized with poly(lysine)-graft-poly(ethylene glycol). In some embodiments, the bottom surface is functionalized with biotinylated bovine serum albumin (BSA).

In some embodiments, the bottom surface is functionalized with a silane comprising an alkyl chain. In some embodiments, the bottom surface is functionalized with a silane comprising an optionally substituted alkyl chain. In some embodiments, the bottom surface is functionalized with a silane comprising a poly(ethylene glycol) chain. In some embodiments, the bottom surface is functionalized with a silane comprising a coupling group. For example the coupling group may comprise chemical moieties, such as amine groups, carboxyl groups, hydroxyl groups, sulfhydryl groups, metals, chelators, and the like. Alternatively, they may include specific binding elements, such as biotin, avidin, streptavidin, neutravidin, lectins, SNAP-TAGs® (self-labeling protein tags) or substrates therefore, associative or binding peptides or proteins, antibodies or antibody fragments, nucleic acids or nucleic acid analogs, or the like. Additionally, or alternatively, the coupling group may be used to couple an additional group that is used to couple or bind with the molecule of interest, which may, in some cases include both chemical functional groups and specific binding elements. By way of example, a coupling group, e.g., biotin, may be deposited upon a substrate surface and selectively activated in a given area. An intermediate binding agent, e.g., streptavidin, may then be coupled to the first coupling group. The molecule of interest, which in this particular example would be biotinylated, is then coupled to the streptavidin.

In some embodiments, the bottom surface is functionalized with a silane comprising biotin, or an analog thereof. In some embodiments, the bottom surface is functionalized with a silane comprising a poly(ethylene) glycol chain, wherein the poly(ethylene glycol) chain comprises biotin. In certain embodiments, the bottom surface is functionalized with a mixture of silanes, wherein at least one type of silane comprises biotin and at least one type of silane does not comprise biotin. In some embodiments, the mixture comprises about 10-fold less, about 25-fold less, about 50-fold less, about 100-fold less, about 250-fold less, about 500-fold less, or about 1000-fold less of the biotinylated silane than the silane not comprising biotin.

Molecules of Interest

In some aspects, the disclosure provides techniques useful for confining a molecule of interest to a desired region of a sample well. In some embodiments, methods described herein involve steps of contacting a sample well having a functionalized surface with a molecule of interest that is configured to bind the functionalized surface.

In some embodiments, the molecule of interest is a polymerizing enzyme. The terms "polymerase" and "polymerizing enzyme," as used herein, generally refer to any enzyme capable of catalyzing a polymerization reaction. Examples of polymerases include, without limitation, a nucleic acid polymerase, a transcriptase or a ligase. A polymerase can be a polymerization enzyme. Embodiments directed towards single molecule nucleic acid extension (e.g., for nucleic acid sequencing) may use any polymerase that is capable of synthesizing a nucleic acid complementary to a target nucleic acid molecule. In some embodiments, a polymerase may be a DNA polymerase, an RNA polymerase, a reverse transcriptase, and/or a mutant or altered form of one or more thereof. In some embodiments, the polymerase can be any polymerase selected from U.S. Provisional Application No. 62/436,410, filed Dec. 19, 2016, the content of which is incorporated herein by reference in its entirety.

In some embodiments, the molecule of interest is a sequencing template. As used herein, a "sequencing template" is a molecule that is the subject of an analysis (e.g., a sequencing analysis). In some embodiments, the sequencing template comprises a nucleic acid molecule. In some embodiments, the nucleic acid molecule is referred to as a "target" or "template" nucleic acid. In some embodiments, the nucleic acid molecule comprises at least one hybridized primer/polymerizing enzyme complex. For example, in some embodiments, the nucleic acid molecule is contacted with a sequencing primer that is complementary to a portion of the nucleic acid molecule such that the sequencing primer anneals to the nucleic acid molecule. This priming location generates a site in which a polymerizing enzyme (e.g., a DNA or RNA polymerase) may couple to the nucleic acid molecule to form a hybridized primer/polymerizing enzyme complex. Accordingly, in some embodiments, the molecule of interest is a sequencing template complex that comprises a template nucleic acid molecule having a hybridized primer/polymerizing enzyme complex.

In some embodiments, the contacting of the sample well with the molecule of interest occurs subsequent to the contacting of the sample well with the functionalizing agent without an intervening wash step.

In some embodiments, the molecule of interest preferentially binds to the functionalized silica surface over the passivated metal oxide surface with about 100-fold to about 1000-fold selectivity, about 200-fold to about 800-fold selectivity, about 400-fold to about 600-fold selectivity, or about 1000-fold to about 2000-fold selectivity. For example, in some embodiments, the molecule of interest preferentially binds to the functionalized silica surface with about 80-fold, 100-fold, 200-fold, 300-fold, 400-fold, 500-fold, 600-fold, 700-fold, 800-fold, 900-fold, 1000-fold, 1100-fold, 1200-fold, 1300-fold, 1400-fold, 1500-fold, 1600-fold, 1700-fold, 1800-fold, 1900-fold, or about 2000-fold or more selectivity.

In some embodiments, selectivity of the molecule of interest for the functionalized silica surface over the passivated metal oxide surface is greater compared to a sample well not contacted with the block copolymer by about 10-fold to about 100-fold, about 50-fold to about 500-fold, about 100-fold to about 1000-fold, or about 200-fold to about 400-fold. For example, in some embodiments, selectivity of the molecule of interest for the functionalized silica surface over the passivated metal oxide surface is greater compared to a sample well not contacted with the block copolymer by about 10-fold, 20-fold, 30-fold, 40-fold, 50-fold, 60-fold, 70-fold, 80-fold, 90-fold, 100-fold, 200-fold, 250-fold, 300-fold, 350-fold, 400-fold, 450-fold, 500- fold, 550-fold, 600-fold, 650-fold, 700-fold, 750-fold, 800-fold, 850-fold, 900-fold, 950-fold, or about 1000-fold or more.

Sample Loading

In some aspects, the present disclosure relates to techniques useful for preparing one or more surfaces of a sample well. For example, in some embodiments, the present disclosure provides methods and compositions for functionalizing a surface of a sample well. A sample comprising one or more compositions described herein may be added to a substrate comprising a sample well by any number of suitable methods. In some embodiments, the sample is loaded by a practitioner, e.g., via a pipette, a dispenser, or any suitable fluid transfer device/system. In some embodiments, the sample is loaded by automated means (e.g., a robotic device/system). In some embodiments, the sample is loaded via one or more microfluidic channels.

In some embodiments, the sample can be delivered to a substrate (e.g., an integrated device comprising sample wells, an array) by methods that are generally used to deliver molecules to an analytical device. For example, delivery methods can include suspending one or more of the compositions described herein in a fluid and flowing the resulting suspension onto a substrate. This can include simply pipetting the relevant suspension onto one or more regions of the substrate, or can include more active flow methods, such as electro-direction or pressure-based fluid flow. In some embodiments, the sample is flowed into selected regions of the substrate, e.g., where a desired surface is to be functionalized in a particular region of a substrate. Regions of a substrate can also be selective targets of delivery simply by pipetting the relevant suspension into the correct region of the substrate. In some embodiments, the reagents, copolymers, molecules, chemicals, compositions, and/or substances described herein are loaded into a sample well in accordance with techniques described in U.S. Provisional Application No. 62/436,407, filed Dec. 19, 2016, the content of which is incorporated herein by reference in its entirety.

As described herein, aspects of the disclosure provide methods of preparing a sample well using one or more of an amphipathic reagent, a block copolymer, a functionalizing agent, and a molecule of interest. In some embodiments, a sample well can be exposed to two or more of these components at approximately the same time. In some embodiments, a sample well is exposed to each of these components in a stepwise fashion. In some embodiments, a sample well is exposed to an amphipathic reagent and a block copolymer at approximately the same time to generate a passivated surface. In some embodiments, a sample well is exposed to an amphipathic reagent prior to the other components to generate a coating layer. In some embodiments, a sample well is exposed to an amphipathic reagent for a period of time that exceeds the period time that the sample well is exposed to a block copolymer. For example, in some embodiments, the amphipathic reagent generates a coating layer through a process of molecular self-assembly that can require a longer incubation period with a sample well having a metal oxide surface.

In some embodiments, a sample well is exposed to an amphipathic reagent for a period of approximately 24 hours to form a coating layer before the sample well is exposed to a block copolymer. In some embodiments, the sample well is exposed to the amphipathic reagent for a period of approximately 4 to 8 hours, approximately 8 to 12 hours, approximately 12 to 16 hours, approximately 16 to 20 hours, approximately 20 to 24 hours, approximately 24 to 28 hours, approximately 28 to 32 hours, approximately 32 to 36 hours, approximately 36 to 40 hours, approximately 40 to 44 hours, approximately 44 to 48 hours or more, to form the coating layer prior to the sample well being exposed to the block copolymer. In some embodiments, a sample well having a coating layer is exposed to a block copolymer for a period of approximately 2 hours before the sample well is exposed to a functionalizing agent. In some embodiments, the sample well having the coating layer is exposed to the block copolymer for a period of approximately 30 minutes, approximately 1 hour, approximately 2 hours, approximately 3 hours, approximately 4 hours, approximately 5 hours, approximately 6 hours, approximately 7 hours, approximately 8 hours or more, to form an antifouling layer over a metal oxide surface.

In some embodiments, a sample well having an antifouling layer is exposed to a functionalizing agent for approximately 1 to 2 hours. In some embodiments, a sample well is exposed to a functionalizing agent for approximately 30 minutes. In some embodiments, a sample well is exposed to a functionalizing agent for approximately 1 hour. In some embodiments, a sample well is exposed to a functionalizing agent for approximately 2 hours. In some embodiments, a sample well is exposed to a functionalizing agent for approximately 30 to 90 minutes. In some embodiments, a sample well is exposed to a functionalizing agent for approximately 3 hours. In some embodiments, a sample well is exposed to a functionalizing agent for more than 3 hours.

In some embodiments, a sample well having a functionalized silica surface is exposed to a molecule of interest for approximately 1 to 2 hours. In some embodiments, a sample well is exposed to a molecule of interest for approximately 30 minutes. In some embodiments, a sample well is exposed to a molecule of interest for approximately 1 hour. In some embodiments, a sample well is exposed to a molecule of interest for approximately 2 hours. In some embodiments, a sample well is exposed to a molecule of interest for approximately 30 to 90 minutes. In some embodiments, a sample well is exposed to a molecule of interest for approximately 3 hours. In some embodiments, a sample well is exposed to a molecule of interest for more than 3 hours.

Sample Preparation

In some embodiments, a sample comprising a target nucleic acid may be extracted from a biological sample obtained from a subject (e.g., a human or other subject). In some embodiments, the subject may be a patient. In some embodiments, a target nucleic acid may be detected and/or sequenced for diagnostic, prognostic, and/or therapeutic purposes. In some embodiments, information for a sequencing assay may be useful to assist in the diagnosis, prognosis, and/or treatment of a disease or condition. In some embodiments, the subject may be suspected of having a health condition, such as a disease (e.g., cancer). In some embodiments, the subject may be undergoing treatment for a disease.

In some embodiments, a biological sample may be extracted from a bodily fluid or tissue of a subject, such as breath, saliva, urine, blood (e.g., whole blood or plasma), stool, or other bodily fluid or biopsy sample. In some examples, one or more nucleic acid molecules are extracted from the bodily fluid or tissue of the subject. The one or more nucleic acids may be extracted from one or more cells obtained from the subject, such as part of a tissue of the subject, or obtained from a cell-free bodily fluid of the subject, such as whole blood.

A biological sample may be processed in preparation for detection (e.g., sequencing). Such processing can include isolation and/or purification of the biomolecule (e.g., nucleic acid molecule) from the biological sample, and generation of more copies of the biomolecule. In some examples, one or more nucleic acid molecules are isolated and purified from a bodily fluid or tissue of the subject, and amplified through nucleic acid amplification, such as polymerase chain reaction (PCR). Then, the one or more nucleic acid molecules or subunits thereof can be identified, such as through sequencing. However, in some embodiments nucleic acid samples can be evaluated (e.g., sequenced) without requiring amplification.

As described in this application, sequencing can include the determination of individual subunits of a template biomolecule (e.g., nucleic acid molecule) by synthesizing another biomolecule that is complementary or analogous to the template, such as by synthesizing a nucleic acid molecule that is complementary to a template nucleic acid molecule and identifying the incorporation of nucleotides with time (e.g., sequencing by synthesis). As an alternative, sequencing can include the direct identification of individual subunits of the biomolecule.

Sequencing

In some aspects, methods and devices described herein may be used in analytical technologies that permit detection of an individual molecule or particle in a sample. The individual molecule may be, by way of example and not limitation, an amino acid, a polypeptide, a nucleotide, a nucleic acid, or a variant thereof comprising a detectable moiety. For example, in some embodiments, methods and compositions provided in the present disclosure may be used in conjunction with single molecule nucleic acid sequencing technologies. Single molecule nucleic acid sequencing allows for the determination of a sequence of a single nucleic acid molecule by monitoring, in real time, the extension of a nucleic acid molecule that is complementary to the template nucleic acid.

In some embodiments, aspects of the present application can be used in methods related to assays of biological samples. In some embodiments, methods provided herein are useful in techniques used to determine the sequence of one or more nucleic acids or polypeptides in the sample and/or to determine the presence or absence of one or more nucleic acid or polypeptide variants (e.g., one or more mutations in a gene of interest) in the sample. In some embodiments, tests can be performed on patient samples (e.g., human patient samples) to provide nucleic acid sequence information or to determine the presence or absence of one or more nucleic acids of interest for diagnostic, prognostic, and/or therapeutic purposes. In some examples, diagnostic tests can include sequencing a nucleic acid molecule in a biological sample of a subject, for example by sequencing cell free DNA molecules and/or expression products (e.g., RNA) in a biological sample of the subject. For example, the present disclosure provides methods and compositions that may be advantageously utilized in the technologies described in co-pending U.S. patent application Ser. Nos. 14/543,865, 14/543,867, 14/543,888, 14/821,656, 14/821,686, 14/821,688, 15/161,067, 15/161,088, 15/161,125, 15/255,245, 15/255,303, 15/255,624, 15/261,697, 15/261,724, 15/600,979, 15/846,967, 15/847,001, 62/289,019, 62/296,546, 62/310,398, 62/339,790, 62/343,997, 62/344,123, 62/426,144, 62/436,407, and 62/436,410, the contents of each of which are incorporated herein by reference.

Some aspects of the application are useful in techniques capable of sequencing biological polymers, such as nucleic acids and proteins. In some embodiments, methods and compositions described in the application can be used in techniques that identify a series of nucleotide or amino acid monomers that are incorporated into a nucleic acid or protein (e.g., by detecting a time-course of incorporation of a series of labeled nucleotide or amino acid monomers). In some embodiments, methods and compositions described in the application can be incorporated into techniques that identify a series of nucleotides that are incorporated into a template-dependent nucleic acid sequencing reaction product synthesized by a polymerizing enzyme in a sample well. In some embodiments, the polymerizing enzyme can be attached to a desired region of the sample well using the highly selective surface functionalization techniques described herein.

In some embodiments a complex comprising a polymerase, a target nucleic acid and a primer is formed in solution and the complex is immobilized to a solid support (e.g., via immobilization of the polymerase, primer, and/or target nucleic acid).

Sample Wells

In some aspects, the disclosure provides an integrated device comprising a substrate comprising a sample well having a metal oxide surface and a silica surface. In some embodiments, the integrated device further comprises a coating layer on the metal oxide surface formed by an amphipathic reagent that comprises a hydrophilic head group and a hydrophobic tail group. In some embodiments, the amphipathic reagent is bound to the metal oxide surface through the hydrophilic head group. In some embodiments, the integrated device further comprises an antifouling overlay on the coating layer formed by an A-B-A type block copolymer that comprises an A block and a B block. In some embodiments, the A-B-A type block copolymer is bound to the coating layer through the B block. In some embodiments, the integrated device further comprises a functionalizing agent bound to the silica surface, wherein the functionalizing agent comprises a coupling moiety.

In some embodiments, the substrate comprises an array of sample wells, each sample well having a metal oxide surface and a silica surface. In some embodiments, the sample well comprises a top aperture formed at a surface of the substrate and a bottom surface distal to the surface of the substrate. In some embodiments, the bottom surface is comprised by the silica surface. In some embodiments, the integrated device is configured to interface with a next-generation sequencing instrument.

As used herein, an "integrated device" is a device capable of interfacing with a base instrument. In some embodiments, an integrated device may comprise one or more sample wells and/or sensors. In some embodiments, an integrated device may be capable of interfacing with a base instrument that emits or detects light. In such embodiments, the integrated device may comprise one or more sample wells, each of which includes a waveguide.

An integrated device of the type described herein may comprise one or more sample wells configured to receive molecules of interest therein. In some embodiments, a sample well receives a molecule of interest that may be disposed on a surface of the sample well, such as a bottom surface. In some embodiments, a sample well is formed within an integrated device, wherein the bottom surface of the sample well is distal to the surface of the integrated device into which it is formed. In some embodiments, the bottom surface on which the molecule of interest is to be disposed may have a distance from a waveguide that is configured to excite the molecule of interest with a desired level of excitation energy. In some embodiments, the sample well may be positioned, with respect to a waveguide, such that an evanescent field of an optical mode propagating along the waveguide overlaps with the molecule of interest.

A sample well may have a top opening at the surface of an integrated device through which a molecule of interest may be placed in the sample well. The size of the top opening may depend on different factors, such as the size of the molecules of interest (e.g., sequencing templates, polymerizing enzymes) in the sample being loaded. In some embodiments, the size of the top opening may depend upon the instrument or apparatus in which integrated device comprising the sample well is being utilized. For example, in devices that detect light from within the sample well, background signals may result from stray light. When a molecule of interest is disposed in the sample well and excited with excitation energy, background signals may cause undesired fluctuations in the emission energy, thus making the measurement noisy. To limit such fluctuations, the size of the top opening may be configured to block at least a portion of the background signals.

The volume of a sample well may be between about $10^{-21}$ liters and about $10^{-15}$ liters, in some implementations. Because the sample well has a small volume, detection of single-sample events (e.g., single-molecule events) may be possible even though molecules of interest may be concentrated in an examined specimen at concentrations that are similar to those found in natural environments. For example, micromolar concentrations of the molecule of interest may be present in a specimen that is placed in contact with the integrated device, but at the pixel level only about one molecule of interest (or single molecule event) may be within a sample well at any given time.

Statistically, some sample wells may contain no molecules of interest and some may contain more than one molecule of interest. However, an appreciable number of sample wells may contain a single molecule of interest (e.g., at least 30% in some embodiments), so that single-molecule analysis can be carried out in parallel for a large number of sample wells. Because single-molecule or single-sample events may be analyzed at each sample well, the integrated device makes it possible to detect individual events that may otherwise go unnoticed in ensemble averages.

EXAMPLES

Example 1. Improved Wettability on Metal Oxide Surface Using Block Copolymer

A process for passivation of a metal oxide surface was evaluated by wettability experiments. A coupon having surface regions composed of $TiO_2$ and $SiO_2$ was subjected to a two-step process that involved the formation of a coating layer and subsequent formation of an antifouling overlay. For the purposes of these experiments, hexylphosphonic acid (HPA) was used to generate the coating layer, and PLURONIC® P123 triblock copolymer ($HO(C_2H_4O)_a$ $(C_3H_6O)_b(C_2H_4O)_aH$) was used to generate the antifouling layer.

The $TiO_2/SiO_2$ coupon was exposed to HPA for a period of 24 hours to allow self-assembly of the HPA monolayer on the $TiO_2$ surface. Following HPA passivation, surface wettability was evaluated by contact angle measurements, with droplets on the $TiO_2$ side of the coupon measuring approximately 85° and droplets on the $SiO_2$ side measuring approximately 15°. A plot of contact angle as a function of time indicated that droplet contact angle remained stable on the HPA-passivated $TiO_2$ surface after two hours.

Following passivation with HPA, the $TiO_2/SiO_2$ coupon was exposed to the triblock copolymer for two hours. Again, contact angle measurements were obtained for each side of the coupon. Wettability on the $SiO_2$ side was seemingly unaffected by the triblock copolymer step, with contact angle maintaining at approximately 15°. This would suggest that the hydrophilicity of $SiO_2$ is unchanged by the addition of block copolymer. In contrast, the $TiO_2$ side of the coupon saw a measurable increase in wettability, with contact angle decreasing to approximately 45°. Imaging of droplets on $TiO_2$ were obtained following the initial HPA passivation (FIG. 6, top) and following exposure of the HPA-passivated surface to the block copolymer (FIG. 6, bottom). The change in wettability here would suggest that the hydrophilicity of HPA-passivated $TiO_2$ is noticeably increased following the addition of block copolymer. Further, these observations would be consistent with the formation of an antifouling overlay formed by the block copolymer.

Example 2. Binding Selectivity Assays to Evaluate Surface Functionalization

Surface selectivity of silanization was evaluated by quantum dot (QD)-streptavidin assays using biotin-conjugated silane on a $TiO_2/SiO_2$ coupon. In these experiments, surface selectivity of the silane compound was examined for either coupons prepared with an HPA-passivated coating only, or with coupons prepared by HPA passivation followed by antifouling overlay with triblock copolymer. Fluorescence imaging results of the different conditions assayed are shown in FIG. 7.

Background fluorescence measurements were obtained using $TiO_2/SiO_2$ coupon that had not been subjected to surface chemistry modification steps (FIG. 7, top). For control experiments, $TiO_2/SiO_2$ coupon was prepared by passivation with HPA followed by surface functionalization with silane-PEG-biotin. Fluorescence measurements were obtained using QD-streptavidin binding assay, which indicated that silanization on the coupon occurred with an approximate 2-fold selectivity for the $SiO_2$ side (FIG. 7, middle). Selectivity was determined by subtracting background fluorescence intensity measurements from control intensity measurements. For example, control selectivity for $SiO_2:TiO_2$ was approximated using the measurements reported in FIG. 7 (top, middle), where selectivity was obtained by: $(Si_{control}-Si_{blank})/(Ti_{control}-Ti_{blank})=(53000-3400)/(25000-2000)=(49600)/(23000)=~2.2$, or approximately 2-fold selectivity.

Next, a $TiO_2/SiO_2$ coupon was prepared as in Example 1, with HPA passivation and triblock copolymer overlay. Following silanization of the copolymer-modified coupon, fluorescence measurements indicated that the silane compound bound to the $SiO_2$ side over the $TiO_2$ side with >500:1 selectivity (FIG. 7, bottom). As shown, the fluorescence signal detected for the $TiO_2$ side of the copolymer coupon approximated the $TiO_2$ side in blank experiments. Accordingly, selectivity was calculated as before, and approximated to demonstrate a greater than 500-fold preference for the $SiO_2$ side.

Example 3. Antifouling Effects in Biological Reactions

The effects of the antifouling overlay on sequencing chips were evaluated by observing fluorescence emissions from dye-labeled nucleotides on chips processed with HPA or HPA/triblock copolymer. As shown in FIG. 8 (left), minimal fluorescence signals were observed in the HPA/triblock copolymer processed chip. Chips processed with HPA only, by contrast, showed far greater emissions detected from the labeled nucleotides in solution (FIG. 8, right). These results indicate that the HPA processed chip was more susceptible to dye-labeled nucleotides being retained within the evanescent volume of the sample well than the HPA/triblock copolymer processed chip. Further, this would suggest that the triblock copolymer confers antifouling properties to minimize or eliminate the susceptibility of dyes sticking to a surface within the evanescent volume. Sequencing reactions were further conducted using the HPA/triblock copolymer processed chip to confirm compatibility with the triblock copolymer surface passivation method (FIG. 9).

EQUIVALENTS AND SCOPE

While several inventive embodiments have been described and illustrated herein, those of ordinary skill in the art will readily envision a variety of other means and/or structures for performing the function and/or obtaining the results and/or one or more of the advantages described herein, and each of such variations and/or modifications is deemed to be within the scope of the inventive embodiments described herein. More generally, those skilled in the art will readily appreciate that all parameters, dimensions, materials, and configurations described herein are meant to be exemplary and that the actual parameters, dimensions, materials, and/or configurations will depend upon the specific application or applications for which the inventive teachings is/are used. Those skilled in the art will recognize, or be able to ascertain using no more than routine experimentation, many equivalents to the specific inventive embodiments described herein. It is, therefore, to be understood that the foregoing embodiments are presented by way of example only and that, within the scope of the appended claims and equivalents thereto, inventive embodiments may be practiced otherwise than as specifically described and claimed. Inventive embodiments of the present disclosure are directed to each individual feature, system, article, material, kit, and/or method described herein. In addition, any combination of two or more such features, systems, articles, materials, kits, and/or methods, if such features, systems, articles, materials, kits, and/or methods are not mutually inconsistent, is included within the inventive scope of the present disclosure.

All definitions, as defined and used herein, should be understood to control over dictionary definitions, definitions in documents incorporated by reference, and/or ordinary meanings of the defined terms.

All references, patents, and patent applications disclosed herein are incorporated by reference with respect to the subject matter for which each is cited, which in some cases may encompass the entirety of the document.

The indefinite articles "a" and "an," as used herein in the specification and in the claims, unless clearly indicated to the contrary, should be understood to mean "at least one."

The phrase "and/or," as used herein in the specification and in the claims, should be understood to mean "either or both" of the elements so conjoined, i.e., elements that are conjunctively present in some cases and disjunctively present in other cases. Multiple elements listed with "and/or" should be construed in the same fashion, i.e., "one or more" of the elements so conjoined. Other elements may optionally be present other than the elements specifically identified by the "and/or" clause, whether related or unrelated to those elements specifically identified. Thus, as a non-limiting example, a reference to "A and/or B", when used in conjunction with open-ended language such as "comprising" can refer, in one embodiment, to A only (optionally including elements other than B); in another embodiment, to B only (optionally including elements other than A); in yet another embodiment, to both A and B (optionally including other elements); etc.

As used herein in the specification and in the claims, "or" should be understood to have the same meaning as "and/or" as defined above. For example, when separating items in a list, "or" or "and/or" shall be interpreted as being inclusive, i.e., the inclusion of at least one, but also including more than one, of a number or list of elements, and, optionally, additional unlisted items. Only terms clearly indicated to the contrary, such as "only one of" or "exactly one of," or, when used in the claims, "consisting of," will refer to the inclusion of exactly one element of a number or list of elements. In general, the term "or" as used herein shall only be interpreted as indicating exclusive alternatives (i.e. "one or the other but not both") when preceded by terms of exclusivity, such as "either," "one of," "only one of," or "exactly one of." "Consisting essentially of," when used in the claims, shall have its ordinary meaning as used in the field of patent law.

As used herein in the specification and in the claims, the phrase "at least one," in reference to a list of one or more elements, should be understood to mean at least one element selected from any one or more of the elements in the list of elements, but not necessarily including at least one of each and every element specifically listed within the list of elements and not excluding any combinations of elements in the list of elements. This definition also allows that elements may optionally be present other than the elements specifically identified within the list of elements to which the phrase "at least one" refers, whether related or unrelated to those elements specifically identified. Thus, as a non-limiting example, "at least one of A and B" (or, equivalently, "at least one of A or B," or, equivalently "at least one of A and/or B") can refer, in one embodiment, to at least one, optionally including more than one, A, with no B present (and optionally including elements other than B); in another embodiment, to at least one, optionally including more than one, B, with no A present (and optionally including elements other than A); in yet another embodiment, to at least one, optionally including more than one, A, and at least one, optionally including more than one, B (and optionally including other elements); etc.

It should also be understood that, unless clearly indicated to the contrary, in any methods claimed herein that include more than one step or act, the order of the steps or acts of the method is not necessarily limited to the order in which the steps or acts of the method are recited.

In the claims, as well as in the specification above, all transitional phrases such as "comprising," "including," "carrying," "having," "containing," "involving," "holding," "composed of," and the like are to be understood to be open-ended, i.e., to mean including but not limited to. Only the transitional phrases "consisting of" and "consisting essentially of" shall be closed or semi-closed transitional phrases, respectively, as set forth in the United States Patent Office Manual of Patent Examining Procedures, Section 2111.03. It should be appreciated that embodiments described in this document using an open-ended transitional phrase (e.g., "comprising") are also contemplated, in alternative embodiments, as "consisting of" and "consisting essentially of" the feature described by the open-ended transitional phrase. For example, if the disclosure describes "a composition comprising A and B," the disclosure also contemplates the alternative embodiments "a composition consisting of A and B" and "a composition consisting essentially of A and B."

The invention claimed is:

1. A method of functionalizing a silica surface of a sample well, the method comprising:
contacting a sample well having a metal oxide surface and a silica surface with an amphipathic reagent, wherein the amphipathic reagent comprises an alkyl phosphonic acid compound of formula $CH_3(CH_2)_nPO_3H_2$, where n is an integer with a value of 1-30, and wherein the amphipathic reagent preferentially binds the metal oxide surface to form a coating layer on the metal oxide surface;
contacting the sample well with a block copolymer, wherein the block copolymer preferentially binds the coating layer on the metal oxide surface and wherein the block copolymer is an A-B-A type block copolymer that comprises an A block and a B block and is a compound of Formula II:

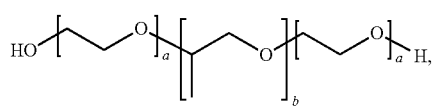
(Formula II)

where:
a is an integer with a value of 2-150; and
b is an integer with a value of 10-100;
contacting the sample well with a functionalizing agent that preferentially binds the silica surface to generate a functionalized silica surface, wherein the functionalizing agent comprises a coupling moiety; and
contacting the sample well having the functionalized silica surface with a molecule of interest that is configured to bind the coupling moiety, under conditions suitable to permit binding of the molecule of interest to the coupling moiety, thereby coupling the molecule of interest to the functionalized silica surface, wherein the contacting of the sample well with the molecule of interest occurs subsequent to the contacting of the sample well with the functionalizing agent without an intervening wash step.

2. The method of claim 1, wherein the hydrophilic head group of the alkyl phosphonic acid compound is configured to preferentially bind the metal oxide surface and the hydrophobic tail group of the alkyl phosphonic acid compound is configured to preferentially bind the block copolymer.

3. The method of claim 1, wherein the coating layer preferentially binds the B block of the A-B-A type block copolymer.

4. The method of claim 1, wherein the metal oxide surface is aluminum oxide, titanium oxide, zirconium oxide, iron oxide, tin oxide, or tantalum oxide.

5. The method of claim 1, wherein the functionalizing agent comprises a silane compound.

6. The method of claim 1, wherein the molecule of interest is a polymerizing enzyme.

7. The method of claim 1, wherein the molecule of interest is a sequencing template complex that comprises a template nucleic acid molecule having a hybridized primer/polymerizing enzyme complex.

8. The method of claim 1, wherein the molecule of interest preferentially binds to the functionalized silica surface over the metal oxide surface with about 100-fold to about 1000-fold selectivity, about 200-fold to about 800-fold selectivity, about 400-fold to about 600-fold selectivity, or about 1000-fold to about 2000-fold selectivity.

9. The method of claim 1, wherein selectivity of the molecule of interest for the functionalized silica surface over the metal oxide surface is greater compared to a sample well not contacted with the block copolymer by about 10-fold to about 100-fold, about 50-fold to about 500-fold, about 100-fold to about 1000-fold, or about 200-fold to about 400-fold.

10. The method of claim 5, wherein the silane compound comprises mono-ethoxysilane, mono-chlorosilane, dichlorosilane, methoxysilane, di-ethoxysilane, trichlorosilane, or di-ethoxy, methoxysilane.

11. The method of claim 1, wherein the coupling moiety of the functionalizing agent comprises a biotin molecule, an avidin protein, a streptavidin protein, a lectin protein, or a SNAP-tag.

12. The method of claim 1, wherein the coupling moiety of the functionalizing agent comprises an amine group, an azido group, a carboxyl group, a hydroxyl group, an alkyl group, an alkyne group, or a sulfhydryl group.

13. The method of claim 1, wherein the amphipathic reagent comprises hexylphosphonic acid, octylphosphonic acid, decylphosphonic acid, dodecylphosphonic acid, polyvinylphosphonic acid, 12-phosphono-1-dodecanesulfonic acid, 10-undecynylphosphonic acid, or heptadecafluorodecylphosphonic acid.

14. The method of claim 13, wherein the amphipathic reagent comprises hexylphosphonic acid.

15. The method of claim 4, wherein the metal oxide surface is titanium oxide.

16. A method of coupling a molecule of interest to a functionalized silica surface, the method comprising:
contacting a functionalized silica surface with a molecule of interest that is configured to bind a coupling moiety of the functionalized silica surface, under conditions suitable to permit binding of the molecule of interest to the coupling moiety, thereby coupling the molecule of interest to the functionalized silica surface, wherein the functionalized silica surface was produced by a method comprising:
contacting a sample well having a metal oxide surface and a silica surface with an amphipathic reagent, wherein the amphipathic reagent comprises an alkyl phosphonic acid compound of formula $CH_3(CH_2)_nPO_3H_2$, where n is an integer with a value of 1-30, and wherein the amphipathic reagent preferentially binds the metal oxide surface to form a coating layer on the metal oxide surface;
contacting the sample well with a block copolymer, wherein the block copolymer preferentially binds the coating layer on the metal oxide surface, and wherein the block copolymer is an A-B-A type block copolymer that comprises an A block and a B block and is a compound of Formula II:

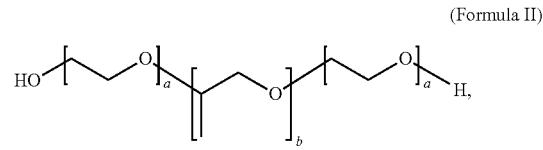
(Formula II)

where:
  a is an integer with a value of 2-150; and
  b is an integer with a value of 10-100; and
contacting the sample well with a functionalizing agent that preferentially binds the silica surface to thereby produce the functionalized silica surface, wherein the functionalizing agent comprises a coupling moiety;
wherein the contacting of the functionalized silica surface with the molecule of interest occurs subsequent to the contacting of the sample well with the functionalizing agent without an intervening wash step.

* * * * *